(12) United States Patent
Breyer et al.

(10) Patent No.: US 8,778,887 B2
(45) Date of Patent: Jul. 15, 2014

(54) THERAPEUTIC USES OF SOLUBLE ALPHA-KLOTHO

(75) Inventors: Matthew Douglas Breyer, Indianapolis, IN (US); Linda Maureen O'Bryan, Indianapolis, IN (US); Rosamund Carol Smith, Greenfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/509,030

(22) PCT Filed: Dec. 15, 2010

(86) PCT No.: PCT/US2010/060436
§ 371 (c)(1),
(2), (4) Date: May 10, 2012

(87) PCT Pub. No.: WO2011/084452
PCT Pub. Date: Jul. 14, 2011

(65) Prior Publication Data
US 2012/0232024 A1    Sep. 13, 2012

Related U.S. Application Data

(60) Provisional application No. 61/286,880, filed on Dec. 16, 2009.

(51) Int. Cl.
*A61K 38/17*    (2006.01)
(52) U.S. Cl.
USPC .......................................................... 514/21.2
(58) Field of Classification Search
None
See application file for complete search history.

(56) References Cited

U.S. PATENT DOCUMENTS 6,579,850 B1    6/2003    Nabeshima et al.
2003/0119910 A1    6/2003    Kamiya et al.

FOREIGN PATENT DOCUMENTS

WO    2009/095372    8/2009

OTHER PUBLICATIONS

Nabeshima Yo-Ichi: "Discovery of alpha-Klotho and FGF23 Unveiled New Insight into Calcium and Phosphate V Homeostasis", Clinical Calcium, Iyaku Janarusha, Osaka, JP, vol. 18, No. 7, Jul. 1, 2008, pp. 923-934.
Imura Akihiro et al: "alpha-Klotho as a Regulator of Calcium Homeostasis", Science, American Association for the Advancement of Science, Washington, DC; US, vol. 316, No. 5831, Jun. 15, 2007, pp. 1615-1618.
Nabeshima Yo-Ichi et al: "alpha-Klotho: a Regulator that Integrates Calcium Homeostasis", American Journal of Nephrology, US National Library of Medicine (NLM), Bethesda, MD; US, vol. 28, No. 3, Jan. 1, 2008, pp. 455-464.
Brownstein Catherine A et al: "A Translocation Causing Increased alpha-Klotho Level Results in Hypophosphatemic Rickets and V Hyperparathyroidism", Proceedings of the National Academy of Sciences of the United States (PNAS), National Academy of Science, US, vol. 105, No. 9, Mar. 4, 2008, pp. 3455-3460.
Sugiura Hidekazu, et al.: "Circulating Levels of Soluble alpha-Klotho in Patients with Chronic Kidney Disease", Clinical Experiments in Nephrology, DOI 10.1007/s10157-011-0511-4, Aug. 5, 2011.
Razzaque, M. Shawkat, "Klotho and Na+,K+-ATPase Activity: Solving the Calcium Metabolism Dilemma?*", Nephrology Dialysis Transplantation, vol. 23, (2008), pp. 459-461.
Hu, Ming Chang, et al., "Klotho: A Novel Phosphaturic Substance Acting as an Autocrine Enzyme in the Renal Proximal Tubule", The FASEB Journal (2010), vol. 24, pp. 1-13.

*Primary Examiner* — Christine J Saoud
(74) *Attorney, Agent, or Firm* — Matthew T. Lord; Andrea M. Castetter

(57) ABSTRACT

The present invention relates to therapeutic uses of soluble alpha-Klotho.

3 Claims, No Drawings

THERAPEUTIC USES OF SOLUBLE ALPHA-KLOTHO

This application is a U.S. national phase entry, pursuant to 35 U.S.C. §371, of PCT/US2010/060436, filed Dec. 15, 2010, which claims the priority of U.S. Provisional Application No. 61/286,880, filed Dec. 16, 2009.

The present invention relates to therapeutic uses of soluble alpha-Klotho.

Alpha-Klotho (aka Klotho) is a 114 kDa protein expressed primarily in the kidney, but also at low levels in other tissues including the parathyroid gland and choroid plexus of the brain. Various endogenous forms of Klotho exist, including a transmembrane form, a soluble form consisting of the extracellular domain which circulates in serum, and at least one soluble splice variant. Klotho is an obligatory partner of FGF23 in terms of both binding and signaling through its cognate FGF receptors, although FGF23-independent activities have been reported. FGF23 is a key regulator of phosphate homeostasis.

Klotho knockout mice develop a variety of kidney and age-related diseases, including tissue calcifications, vascular calcification, and osteopenia. Ectopic expression of the full-length Klotho protein in Klotho knockout mice can reverse many of these phenotypes. Adenoviral overexpression of transmembrane Klotho in various mouse models of renal disease produces beneficial effects. Renal Klotho expression decreases in patients with chronic kidney disease.

A Klotho translocation in man resulting in increased levels of serum Klotho is associated with hypophosphatemia, increased serum FGF23 and PTH levels, and rickets. An hypomorphic Klotho mutation in man was associated with hyperphosphatemia, increased serum FGF23 levels, and tumoral calcinosis. This has led to the hypothesis that chronic kidney disease and perhaps other age-related diseases may represent a state of Klotho insufficiency. Although anti-apoptotic/proliferative activities of the extracellular domain of Klotho in vitro have been reported, there are no published reports to date demonstrating an activity of a soluble form of Klotho in vivo, except for an effect recently reported on potassium excretion.

Human and mouse alpha-Klotho polypeptides are disclosed in U.S. Pat. No. 6,579,850. PCT application WO 2009/095372 discloses compositions for preventing or treating age-related conditions or metabolic disorders using Klotho fusion polypeptides comprising a Klotho protein and a fibroblast growth factor (FGF).

An objective for the present invention is to provide a simple therapeutic paradigm with flexibility and control in terms of dosing and reduced chance for exogenous drug-drug interactions. Many states of hyperphosphatemia, such as chronic kidney disease, are associated with increased FGF23 levels. Therefore, it is possible that administration of exogenous FGF23 (alone or in fusion forms) may be detrimental in certain situations. Delivery of soluble alpha-Klotho may be advantageous. The present invention derives from the surprising observations that soluble alpha-Klotho expressed in vivo is hypophosphatemic and moreover does not require exogenous FGF23 (intact or fused with Klotho) for its in vivo hypophosphatemic activities and results in an up-regulation of endogenous FGF23 levels (many-fold molar excess compared to soluble Klotho), which suggests that it might be important to keep in vivo FGF23-Klotho levels correctly balanced.

Thus, the present invention provides a method of treating or preventing hyperphosphatemia or calcinosis, hyperphosphatemia and calcinosis, chronic renal disease or chronic renal failure, chronic renal disease and chronic renal failure, tissue or vascular calcification, tissue and vascular calcification, albuminuria or proteinuria, or albuminuria and proteinuria in a patient, comprising administering to the patient an effective amount of soluble alpha-Klotho.

The present invention will be useful as a therapeutic approach where endogenous Klotho is insufficient and/or FGF23 levels are perturbed from normal. These conditions include kidney disease, tissue and vascular calcifications, hyperphosphatemia, osteopenia (particularly loss of BMD of cortical bone), and diseases or conditions exhibited by Klotho knockout mice, including arteriosclerosis, infertility, short life span, pulmonary emphysema, skin atrophy, anemia, thymic atrophy, ectopic calcifications including those of the kidney and vasculature, accumulation of renal interstitial matrix, glomerulosclerosis, and neuronal degeneration.

Additional examples of possible Klotho insufficiency include cancer, diabetes, heart disease, vascular disease, lung disease, bone disease, Parkinson's Disease, Alzheimer's Disease, Multiple Sclerosis, cachexia and Muscular Dystrophy.

The present invention also provides a method of reducing blood pressure or calcific atherosclerotic plaque burden, or reducing blood pressure and calcific atherosclerotic plaque burden in a patient, comprising administering an effective amount of soluble alpha-Klotho to the patient; a method of lowering serum phosphate levels in a patient, comprising administering an effective amount of soluble alpha-Klotho to the patient; a method of increasing FGF23 in a patient, comprising administering an effective amount of soluble alpha-Klotho to the patient; use of soluble alpha-Klotho in the manufacture of a medicament for treating or preventing hyperphosphatemia or calcinosis, hyperphosphatemia and calcinosis, chronic renal disease or chronic renal failure, chronic renal disease and chronic renal failure, tissue or vascular calcification, tissue and vascular calcification, albuminuria or proteinuria, or albuminuria and proteinuria; use of soluble alpha-Klotho in the manufacture of a medicament for reducing blood pressure or calcific atherosclerotic plaque burden, or reducing blood pressure and calcific atherosclerotic plaque burden; use of soluble alpha-Klotho in the manufacture of a medicament for lowering serum phosphate levels; use of soluble alpha-Klotho in the manufacture of a medicament for increasing FGF23; use of soluble alpha-Klotho in treating or preventing hyperphosphatemia or calcinosis, hyperphosphatemia and calcinosis, chronic renal disease or chronic renal failure, chronic renal disease and chronic renal failure, tissue or vascular calcification, tissue and vascular calcification, albuminuria or proteinuria, or albuminuria and proteinuria; use of soluble alpha-Klotho in reducing blood pressure or calcific atherosclerotic plaque burden, or reducing blood pressure and calcific atherosclerotic plaque burden; use of soluble alpha-Klotho in lowering serum phosphate levels; and use of soluble alpha-Klotho in increasing FGF23.

Soluble alpha-Klotho is selected from the group consisting of SEQ ID NO: 11, SEQ ID NO: 5, SEQ ID NO: 7, and SEQ ID NO: 9; most preferably, SEQ ID NO: 5.

The term "soluble alpha-Klotho" as used herein, refers to soluble active fragments of Klotho or the extracellular domain (ECD) of Klotho, including soluble human Klotho (SEQ ID NO: 4), soluble rat Klotho (SEQ ID NO: 6), soluble mouse Klotho (SEQ ID NO: 1), soluble monkey Klotho (SEQ ID NO: 8), human Klotho extracellular domain (ECD) (SEQ ID NO: 5), rat Klotho ECD (SEQ ID NO: 7), mouse Klotho ECD (SEQ ID NO: 11), and monkey Klotho ECD (SEQ ID NO: 9).

The term "treating" (or "treat" or "treatment") means slowing, stopping, reducing, or reversing the progression or severity of a symptom, disorder, condition, or disease.

The term "preventing" (or "prevent" or "prevention") refers to a decrease in the occurrence of a symptom, disorder, condition, or disease or decrease in the risk of acquiring a symptom, disorder, condition, or disease or its associate symptoms in a subject.

A "patient" is a mammal, preferably a human.

The term "effective amount" refers to the amount or dose of soluble alpha-Klotho, which provides the desired treatment upon single or multiple dose administration to a patient.

EXAMPLE

Effects of AAV8-mediated Soluble Klotho Overexpression in Normal Mice

The in vivo effects of elevated soluble Klotho levels in serum are assessed in the following studies. Overexpression of Klotho is confirmed by directly measuring mouse serum Klotho levels by enzyme-linked immunosorbent assay (ELISA). Effects of Klotho overexpression on serum phosphate, calcium, FGF23 and PTH are examined.

To induce an increase in serum Klotho levels, an adenoviral system is employed. The extracellular domain (ECD) of mouse Klotho protein with a CD33 N-terminal signal sequence (SEQ ID NO: 2) is packaged into a recombinant hybrid adeno-associated viral vector 2/8 (AAV8). Expression of Klotho is driven by a liver-specific thyroxine binding globulin (TBG) promoter.

Normal male C57Bl6 mice are used in this study at 8-9 weeks of age. Mice are given a single retro-orbital injection of vehicle, or virus (mouse Klotho ECD with a CD33 N-terminal signal sequence (SEQ ID NO: 2) or LacZ control (SEQ ID NO: 3)). Viral dose range for Klotho ECD is $1 \times 10^{10}$ to $1 \times 10^{11}$ genomic copies per mouse. Serum is obtained from the mice at 2, 4 and 8 weeks. A subset of mice is sacrificed at week 2. The remaining mice are bled at week 4 and at the time of sacrifice (week 8).

Mouse Klotho ELISA

Mouse Klotho protein in mouse serum is measured in a sandwich ELISA assay, in which mouse Klotho is captured with an antibody coated on a plate, then captured Klotho is measured using a labeled second antibody.

Each well of a 96-well plate is coated with 70 µL of goat anti-mouse Klotho polyclonal capture antibody (R&D Systems AF1819, 2 µg/mL in carbonate buffer, pH 9.6). Standard curve is run in triplicate, while samples are run in duplicate. The plate is sealed and incubated at 4° C. overnight. The wells are aspirated and washed twice with washing buffer (20 mM Tris (hydroxymethyl) aminomethane, pH 7.4, 0.15 M NaCl, 0.1% Tween-20), using an automatic plate washer. The plates are blocked with 200 µL blocking buffer per well (5% Carnation Instant milk in the above washing buffer) for 1-4 hours at room temperature.

Mouse serum samples are diluted in SeraSub® (CST Technologies) at a 1:2 dilution. Standards are prepared with mouse Klotho ECD (SEQ ID NO: 10), diluted in 50% SeraSub®, 50% pooled mouse serum (Bioreclamation, catalog #MSESRM), such that the standard curve diluent contains the same proportion of mouse serum to SeraSub® as the samples. Next, 50 µL of each sample is added to the antibody-coated wells in duplicate (or triplicate, in the case of the standards). The plates are incubated for 1.5 hours at room temperature. The wells are then washed 3 times with washing buffer.

Biotinylated anti-Klotho antibody (50 µL biotinylated goat anti-mouse Klotho polyclonal, diluted to 2 µg/mL in blocking buffer) is added to each well and incubated for 45 minutes at room temperature. The wells are then washed 3 times with washing buffer. Then, 50 µL of peroxidase-conjugated streptavidin is added to the wells, and the plate is incubated for 30 minutes at room temperature. Next, 50 µL of chromogenic substrate (i.e., OPD substrate, Sigma, catalog #P-6912) is added to each well and allowed to develop at room temperature for 2-4 minutes. The reaction is stopped by adding 100 µL 1N HCl to each well. The absorbance of the wells is read at 490 nm on a Molecular Devices SpectraMax250 plate reader. The average absorbance from duplicate wells is determined, back-calculations for dilutions are made, and the resulting values are listed in Table 1, below.

Intact FGF23 ELISA

Intact FGF23 levels are measured using a commercially-available human intact FGF23 ELISA kit (Kainos Laboratories, catalog #CY-4000). Manufacturer's instructions are followed. Sera are diluted at various concentrations such that the values are within the range of the standard curve for quantification. Standard curve ranges from 3-800 pg/mL. The assumption is made that the ELISA has 100% cross-reactivity to mouse Klotho. The average absorbance from duplicate wells is determined, back-calculations for dilutions are made, and the resulting values are listed in Table 1, below.

Intact PTH ELISA

Intact PTH levels are measured using a commercially-available mouse intact PTH ELISA kit (Immutopics, catalog #60-2300). Manufacturer's instructions are followed, with the exception that only 1 replicate is measured. Standard curve ranges from 36-3500 pg/mL. Results are listed in Table 1, below.

Serum Phosphate and Calcium Measurements

Serum is collected and analyzed for calcium and inorganic phosphorous. Calcium levels are determined by a colorimetric method in which o-cresolphthalein complexone reacts with calcium in the sample at alkaline pH to form calcium-o-cresolphthalein complex. The calcium concentration is directly proportional to the color intensity of this complex and is photometrically measured with an automated chemistry analyzer. Inorganic phosphorous combines with ammonium molybdate under acidic conditions to form an ammonium molybdate complex. The concentration of this complex is also measured photometrically. Roche Calcium and Inorganic Phosphorous reagent kits are utilized for this analysis, as well as either a Hitachi 912 or Hitachi Modular Analytics Chemistry analyzer (Roche Diagnostics). Results are listed in Table 1, below.

TABLE 1

| group GC/mouse | Klotho ng/mL | Phosphate mg/dL | Calcium mg/dL | FGF23 pg/mL | PTH pg/mL |
| --- | --- | --- | --- | --- | --- |
| Week 2 | | | | | |
| vehicle | nd1 | 6.9 (0.4) | 10.0 (0.2) | 66 (10) | nd2 |
| LacZ control | nd1 | 7.0 (0.2) | 9.9 (0.1) | 92 (9)* | nd2 |
| $1 \times 10^{10}$ | 112 (19)* | 7.1 (0.5) | 10.3 (0.1)* | 106 (12)* | nd2 |

TABLE 1-continued

| group GC/mouse | Klotho ng/mL | Phosphate mg/dL | Calcium mg/dL | FGF23 pg/mL | PTH pg/mL |
|---|---|---|---|---|---|
| 3 × 10¹⁰ | 37 (25) | 5.4 (0.5)* | 10.1 (0.3) | 1330 (1131) | 58 (36)* |
| 1 × 10¹¹ | 107 (18)* | 3.6 (0.5)* | 9.8 (0.1) | 53248 (30447)* | 146 (84)* |
| Week 4 | | | | | |
| vehicle | nd1 | 7.3 (0.3) | 9.8 (0.1) | (i.s.) | (i.s.) |
| LacZ control | 30 (3)* | 7.2 (0.9) | 9.7 (0.1) | (i.s.) | (i.s.) |
| 1 × 10¹⁰ | 55 (23)* | 7.1 (0.3) | 9.8 (0.2) | (i.s.) | (i.s.) |
| 3 × 10¹⁰ | 75 (5)* | 4.2 (0.4)* | 9.3 (0.3)* | (i.s.) | (i.s.) |
| 1 × 10¹¹ | 142 (22)* | 3.2 (0.4)* | 9.4 (0.1)* | (i.s.) | (i.s.) |
| Week 8 | | | | | |
| vehicle | 5 (5) | 7.6 (0.4) | 9.8 (0.3) | 97 (46) | 122 (10) |
| LacZ control | 7 (10) | 7.5 (0.5) | 9.7 (0.1) | 56 (8) | 115 (11) |
| 1 × 10¹⁰ | 30 (4)* | 7.5 (0.5) | 9.7 (0.2) | 106 (41) | 119 (21) |
| 3 × 10¹⁰ | 37 (13)* | 5.9 (0.6)* | 9.4 (0.3)* | 3677 (2427)* | 271 (92)* |
| 1 × 10¹¹ | 62 (17)* | 4.6 (0.5)* | 9.0 (0.3)* | 17854 (5463)* | 477 (182)* | average (standard deviation) listed,
*denotes statistical significance
student's t-test, p < 0.05, n = 2-5 samples
nd1 denotes not detectable, lower limit of detection = 12-37 ng/mL
nd2 denotes not detectable, lower limit of detection = 36 pg/mL
(i.s.) = insufficient serum available to perform assay
GC = genomic copies Serum levels of Klotho (determined by ELISA) in vehicle-treated mice in this study are in the range of those reported in the literature [Kurosu et al., Science, 2005]. Overexpression of soluble Klotho is achieved, through use of an AAV2/8 system, compared to serum Klotho levels in vehicle-treated mice. While the amplitude of the increase in serum levels of Klotho appears to decline over time, levels remain elevated compared to vehicle throughout the study. The maximum increase of Klotho serum levels measured in this study was approximately 24-fold over vehicle. Serum levels of FGF23 are statistically significantly increased in mice with elevated serum Klotho levels (maximal increase approximately 807-fold). The increase in serum FGF23 persists throughout the study. PTH levels are elevated at both the week 2 and 8 time points (week 4 not tested) in mice over-expressing soluble Klotho. Serum phosphate levels are statistically significantly and dose-responsively reduced at all time points, with maximal reduction of approximately 56% from vehicle. These data demonstrate that increased soluble Klotho serum levels lead to a decrease in levels of serum phosphate. Serum calcium is slightly but statistically significantly elevated early at the lowest dose (week 2) compared to vehicle, then is reduced at weeks 4 and 8 in mice over-expressing serum soluble Klotho (maximal reduction approximately 8%).

A repeat study of similar design confirmed that administration of soluble Klotho via AAV2/8 (viral dose ranging from 1×10⁹ to 3×10¹¹ genomic copies per mouse) resulted in increased serum Klotho levels (levels as high as 800 ng/mL), increased serum FGF23 levels, and decreased serum phosphate and calcium. PTH was only measured at weeks 10 and 12, at which times no significant changes were observed.

```
Mouse Klotho
                                            (SEQ ID NO: 1)
MLARAPPRRPPRLVLLRLLLLHLLLLALRARCLSAEPGQGAQTWARFARA

PAPEAAGLLHDTFPDGFLWAVGSAAYQTEGGWRQHGKGASIWDTFTHHSG

AAPSDSPIVVAPSGAPSPPLSSTGDVASDSYNNVYRDTEGLRELGVTHYR

FSISWARVLPNGTAGTPNREGLRYYRRLLERLRELGVQPVVTLYHWDLPQ

RLQDTYGGWANRALADHFRDYAELCFRHFGGQVKYWITIDNPYVVAWHGY
```

```
                            -continued
ATGRLAPGVRGSSRLGYLVAHNLLLAHAKVWHLYNTSFRPTQGGRVSIAL

SSHWINPRRMTDYNIRECQKSLDFVLGWFAKPIFIDGDYPESMKNNLSSL

LPDFTESEKRLIRGTADFFALSFGPTLSFQLLDPNMKFRQLESPNLRQLL

SWIDLEYNHPPIFIVENGWFVSGTTKRDDAKYMYYLKKFIMETLKAIRLD

GVDVIGYTAWSLMDGFEWHRGYSIRRGLFYVDFLSQDKELLPKSSALFYQ

KLIEDNGFPPLPENQPLEGTFPCDFAWGVVDNYVQVDTTLSQFTDPNVYL

WDVHHSKRLIKVDGVVAKKRKPYCVDFSAIRPQITLLREMRVTHFRFSLD

WALILPLGNQTQVNHTVLHFYRCMISELVHANITPVVALWQPAAPHQGLP

HALAKHGAWENPHTALAFADYANLCFKELGHWVNLWITMNEPNTRNMTYR

AGHHLLRAHALAWHLYDDKFRAAQKGKISIALQADWIEPACPFSQNDKEV

AERVLEFDIGWLAEPIFGSGDYPRVMRDWLNQKNNFLLPYFTEDEKKLVR

GSFDFLAVSHYTTILVDWEKEDPMKYNDYLEVQEMTDITWLNSPSQVAVV

PWGLRKVLNWLRFKYGDLPMYVTANGIDDDPHAEQDSLRIYYIKNYVNEA

LKAYVLDDINLCGYFAYSLSDRSAPKSGFYRYAANQFEPKPSMKHYRRII

DSNGFLGSGTLGRFCPEEYTVCTECGFFQTRKSLLVFISF

LVFTFIISLA LIFHYSKKGQRSYK

Mouse Klotho Extracellular Domain (ECD) -
CD33 N-terminal Signal Sequence
                                           (SEQ ID NO: 2)
MPLLLLLPLLWAGALAMAEPGQGAQTWARFARAPAPEAAGLLHDTFPDGF

LWAVGSAAYQTEGGWRQHGKGASIWDTFTHHSGAAPSDSPIVVAPSGAPS

PPLSSTGDVASDSYNNVYRDTEGLRELGVTHYRFSISWARVLPNGTAGTP

NREGLRYYRRLLERLRELGVQPVVTLYHWDLPQRLQDTYGGWANRALADH

FRDYAELCFRHFGGQVKYWITIDNPYVVAWHGYATGRLAPGVRGSSRLGY

LVAHNLLLAHAKVWHLYNTSFRPTQGGRVSIALSSHWINPRRMTDYNIRE

CQKSLDFVLGWFAKPIFIDGDYPESMKNNLSSLLPDFTESEKRLIRGTAD
```

-continued

FFALSFGPTLSFQLLDPNMKFRQLESPNLRQLLSWIDLEYNHPPIFIVEN
GWFVSGTTKRDDAKYMYYLKKFIMETLKAIRLDGVDVIGYTAWSLMDGFE
WHRGYSIRRGLFYVDFLSQDKELLPKSSALFYQKLIEDNGFPPLPENQPL
EGTFPCDFAWGVVDNYVQVDTTLSQFTDPNVYLWDVHHSKRLIKVDGVVA
KKRKPYCVDFSAIRPQITLLREMRVTHFRFSLDWALILPLGNQTQVNHTV
LHFYRCMISELVHANITPVVALWQPAAPHQGLPHALAKHGAWENPHTALA
FADYANLCFKELGHWVNLWITMNEPNTRNMTYRAGHHLLRAHALAWHLYD
DKFRAAQKGKISIALQADWIEPACPFSQNDKEVAERVLEFDIGWLAEPIF
GSGDYPRVMRDWLNQKNNFLLPYFTEDEKKLVRGSFDFLAVSHYTTILVD
WEKEDPMKYNDYLEVQEMTDITWLNSPSQVAVVPWGLRKVLNWLRFKYGD
LPMYVTANGIDDDPHAEQDSLRIYYIKNYVNEALKAYVLDDINLCGYFAY
SLSDRSAPKSGFYRYAANQFEPKPSMKHYRKIIDSNGFLGSGTLGRFCPE
EYTVCTECGFFQTRKS

LacZ Control
(SEQ ID NO: 3)
MTMITDSLAVVLQRRDWENPGVTQLNRLAAHPPFASWRNSEEARTDRPSQ
QLRSLNGEWRFAWFPAPEAVPESWLECDLPEADTVVVPSNWQMHGYDAPI
YTNVTYPITVNPPFVPTENPTGCYSLTFNVDESWLQEGQTRIIFDGVNSA
FHLWCNGRWVGYGQDSRLPSEFDLSAFLRAGENRLAVMVLWSDGSYLEDQ
DMWRMSGIFRDVSLLHKPTTQISDFHVATRFNDDFSRAVLEAEVQMCGEL
RDYLRVTVSLWQGETQVASGTAPFGGEIIDERGGYADRVTLRLNVENPKL
WSAEIPNLYRAVVELHTADGTLIEAEACDVGFREVRIENGLLLLNGKPLL
IRGVNRHEHHPLHGQVMDEQTMVQDILLMKQNNFNAVRCSHYPNHPLWYT
LCDRYGLYVVDEANIETHGMVPMNRLTDDPRWLPAMSERVTRMVQRDRNH
PSVIIWSLGNESGHGANHDALYRWIKSVDPSRPVQYEGGGADTTATDIIC
PMYARVDEDQPFPAVPKWSIKKWLSLPGETRPLILCEYAHAMGNSLGGFA
KYWQAFRQYPRLQGGFVWDWVDQSLIKYDENGNPWSAYGGDFGDTPNDRQ
FCMNGLVFADRTPHPALTEAKHQQQFFQFRLSGQTIEVTSEYLFRHSDNE
LLHWMVALDGKPLASGEVPLDVAPQGKQLIELPELPQPESAGQLWLTVRV
VQPNATAWSEAGHISAWQQWRLAENLSVTLPAASHAIPHLTTSEMDFCIE
LGNKRWQFNRQSGFLSQMWIGDKKQLLTPLRDQFTRAPLDNDIGVSEATR
IDPNAWVERWKAAGHYQAEAALLQCTADTLADAVLITTAHAWQHQGKTLF
ISRKTYRIDGSGQMAITVDVEVASDTPHPARIGLNCQLAQVAERVNWLGL
GPQENYPDRLTAACFDRWDLPLSDMYTPYVFPSENGLRCGTRELNYGPHQ
WRGDFQFNISRYSQQQLMETSHRHLLHAEEGTWLNIDGFHMGIGGDDSWS
PSVSAEFQLSAGRYHYQLVWCQK Human Klotho
(SEQ ID NO: 4)
MPASAPPRRPRPPPPSLSLLLVLLGLGGRRLRAEPGDGAQTWARVSRPPA
PEAAGLFQGTFPDGFLWAVGSAAYQTEGGWQQHGKGASIWDTFTHPLAPP
GDSRNASLPLGAPSPLQPATGDVASDSYNNVFRDTEALRELGVTHYRFSI
SWARVLPNGSAGVPNREGLRYYRRLLERLRELGVQPVVTLYHWDLPQRLQD
AYGGWANRALADHFRDYAELCFRHFGGQVKYWITIDNPYVVAWHGYATGR
LAPGIRGSPRLGYLVAHNLLLAHAKVWHLYNTSFRPTQGGQVSIALSSHW
INPRRMTDHSIKECQKSLDFVLGWFAKPVFIDGDYPESMKNNLSSILPDF
TESEKKFIKGTADFFALCFGPTLSFQLLDPHMKFRQLESPNLRQLLSWID
LEFNHPQIFIVENGWFVSGTTKRDDAKYMYYLKKFIMETLKAIKLDGVDV
IGYTAWSLMDGFEWHRGYSIRRGLFYVDFLSQDKMLLPKSSALFYQKLIE
KNGFPPLPENQPLEGTFPCDFAWGVVDNYIQVDTTLSQFTDLNVYLWDVH
HSKRLIKVDGVVTKKRKSYCVDFAAIQPQIALLQEMHVTHFRFSLDWALI
LPLGNQSQVNHTILQYYRCMASELVRVNITPVVALWQPMAPNQGLPRLLA
RQGAWENPYTALAFAEYARLCFQELGHHVKLWITMNEPYTRNMTYSAGHN
LLKAHALAWHVYNEKFRHAQNGKISIALQADWIEPACPFSQKDKEVAERV
LEFDIGWLAEPIFGSGDYPWVMRDWLNQRNNFLLPYFTEDEKKLIQGTFD
FLALSHYTTILVDSEKEDPIKYNDYLEVQEMTDITWLNSPSQVAVVPWGL
RKVLNWLKFKYGDLPMYIISNGIDDGLHAEDDQLRVYYMQNYINEALKAH
ILDGINLCGYFAYSFNDRTAPRFGLYRYAADQFEPKASMKHYRKIIDSNG
FPGPETLERFCPEEFTVCTECSFFHTRKSLLAFIAFLFFASIISLSLIFY
YSKKGRRSYK Human Klotho ECD
(SEQ ID NO: 5)
MPASAPPRRPRPPPPSLSLLLVLLGLGGRRLRAEPGDGAQTWARVSRPPA
PEAAGLFQGTFPDGFLWAVGSAAYQTEGGWQQHGKGASIWDTFTHHPLAP
PGDSRNASLPLGAPSPLQPATGDVASDSYNNVFRDTEALRELGVTHYRFS
ISWARVLPNGSAGVPNREGLRYYRRLLERLRELGVQPVVTLYHWDLPQRL
QDAYGGWANRALADHFRDYAELCFRHFGGQVKYWITIDNPYVVAWHGYAT
GRLAPGIRGSPRLGYLVAHNLLLAHAKVWHLYNTSFRPTQGGQVSIALSS
HWINPRRMTDHSIKECQKSLDFVLGWFAKPVFIDGDYPESMKNNLSSILP
DFTESEKKFIKGTADFFALCFGPTLSFQLLDPHMKFRQLESPNLRQLLSW
IDLEFNHPQIFIVENGWFVSGTTKRDDAKYMYYLKKFIMETLKAIKLDGV
DVIGYTAWSLMDGFEWHRGYSIRRGLFYVDFLSQDKMLLPKSSALFYQKL
IEKNGFPPLPENQPLEGTFPCDFAWGVVDNYIQVDTTLSQFTDLNVYLWD
VHHSKRLIKVDGVVTKKRKSYCVDFAAIQPQIALLQEMHVTHFRFSLDWA
LILPLGNQSQVNHTILQYYRCMASELVRVNITPVVALWQPMAPNQGLPRL
LARQGAWENPYTALAFAEYARLCFQELGHHVKLWITMNEPYTRNMTYSAG
HNLLKAHALAWHVYNEKFRHAQNGKISIALQADWIEPACPFSQKDKEVAE
RVLEFDIGWLAEPIFGSGDYPWVMRDWLNQRNNFLLPYFTEDEKKLIQGT
FDFLALSHYTTILVDSEKEDPIKYNDYLEVQEMTDITWLNSPSQVAVVPW
GLRKVLNWLKFKYGDLPMYIISNGIDDGLHAEDDQLRVYYMQNYINEALK
AHILDGINLCGYFAYSFNDRTAPRFGLYRYAADQFEPKASMKHYRKIIDS
NGFPGPETLERFCPEEFTVCTECSFFHTRKS Rat Klotho
(SEQ ID NO: 6)
MPARAPPRRLPRLLLLRLLSLHLLLLTLRARCLSAEPGQGAQTWARFARP
PVPEASGLLHDTFPDGFLWAVGSAAYQTEGGWRQHGKGASIWDTFTHHPR -continued

AIPEDSPIVMAPSGAPLPPLPSTGDVASDSYNNVYRDTEGLRELGVTHYR

FSISWARVLPNGTAGTPNREGLRYYRRLLERLRELGVQPVVTLYHWDLPQ

RLQDTYGGWANRALADHFRDYAELCFRHFGGQVKYWITIDNPYVVAWHGY

ATGRLAPGVRGSSRLGYLVAHNLLLAHAKVWRLYNTSFRPTQGGRVSIAL

GSHWITPRRMTDYHIRECQKSLDFVLGWFAKPIFIDGDYPKSMKNNLSSL

LPDFTESEKRFIRGTADFFALSFGPTLSFQLLDPSMKFRQLESPSLRQLL

SWIDLEYNHPQIFIVENGWFVSGTTRRDDAKYMYYLKKFIMESLKAIRLD

GVDVIGYTAWSLMDGFEWHRGYSIRRGLFYVDFLSQDKELLPKSSALFYQ

KLIENNGFPPLPENQPLEGTFPCDFAWGVVDNYIQVDPTLSQFTDPNVYL

WDVHHSKRLIKVDGVVAKKRKPYCVDFSAIRPQITLLREMRVTHFRFSLD

WALILPLGNQTQVNRTVLHFYRCMVSELVHANITPVVALWQPATPHQGLP

HALAKHGAWENPHTALAFADYANLCFEELGHWVKFWITINEPNSRNMTYR

AGHHLLKAHALAWHLYDDKFRAAQKGKISIALQVDWIEPACPFSQKDKEV

AERVLEFDVGWLAEPIFGSGDYPHVMREWLNQKNNFLLPYFTEDEKKLIR

GSFDFLALSHYTTILVDWEKEDPIKYNDYLEVQEMTDITWLNSPNQVAVV

PWGLRKALNWLRFKYGDLPMFVTANGIDDDPHAEQDSLRMYYIKNYVNEA

LKAYVLDGINLCGYFAYSLSDRSVPKSGFYRYAANQFEPKPSIKHYRKII

DNNGFLGSGTLGRFCPEEYTVCTGCGFFQTRKSLLAFISFLVFAFVTSLA

LIYYYSKKGRRRYK

Rat Klotho ECD (SEQ ID NO: 7)

MPARAPPRRLPRLLLLRLLSLHLLLLTLRARCLSAEPGQGAQTWARFARP

PVPEASGLLHDTFPDGFLWAVGSAAYQTEGGWRQHGKGASIWDTFTHHPR

AIPEDSPIVMAPSGAPLPPLPSTGDVASDSYNNVYRDTEGLRELGVTHYR

FSISWARVLPNGTAGTPNREGLRYYRRLLERLRELGVQPVVTLYHWDLPQ

RLQDTYGGWANRALADHFRDYAELCFRHFGGQVKYWITIDNPYVVAWHGY

ATGRLAPGVRGSSRLGYLVAHNLLLAHAKVWRLYNTSFRPTQGGRVSIAL

GSHWITPRRMTDYHIRECQKSLDFVLGWFAKPIFIDGDYPKSMKNNLSSL

LPDFTESEKRFIRGTADFFALSFGPTLSFQLLDPSMKFRQLESPSLRQLL

SWIDLEYNHPQIFIVENGWFVSGTTRRDDAKYMYYLKKFIMESLKAIRLD

GVDVIGYTAWSLMDGFEWHRGYSIRRGLFYVDFLSQDKELLPKSSALFYQ

KLIENNGFPPLPENQPLEGTFPCDFAWGVVDNYIQVDPTLSQFTDPNVYL

WDVHHSKRLIKVDGVVAKKRKPYCVDFSAIRPQITLLREMRVTHFRFSLD

WALILPLGNQTQVNRTVLHFYRCMVSELVHANITPVVALWQPATPHQGLP

HALAKHGAWENPHTALAFADYANLCFEELGHWVKFWITINEPNSRNMTYR

AGHHLLKAHALAWHLYDDKFRAAQKGKISIALQVDWIEPACPFSQKDKEV

AERVLEFDVGWLAEPIFGSGDYPHVMREWLNQKNNFLLPYFTEDEKKLIR

GSFDFLALSHYTTILVDWEKEDPIKYNDYLEVQEMTDITWLNSPNQVAVV

PWGLRKALNWLRFKYGDLPMFVTANGIDDDPHAEQDSLRMYYIKNYVNEA

LKAYVLDGINLCGYFAYSLSDRSVPKSGFYRYAANQFEPKPSIKHYRKII

DNNGFLGSGTLGRFCPEEYTVCTGCGFFQTRKS

Monkey Klotho (SEQ ID NO: 8)

MPASAPPRRPRPPPPSLSLSLLLVLLGLAGRRLRAEPGDGAQTWARFARP

PAPEAAGLFQGTFPDGFLWAVGSAAYQTEGGWQQHGKGASIWDTFTHHPL

APPGDSRIANVPSGAPSPLQPATGDVASDSYNNVFRDTEALRELGVTHYR

FSISWARVLPNGSAGVPNREGLRYYRRLLERLRELGVQPVVTLYHWDLPQ

RLQDAYGGWANRALADHFRDYAELCFRHFGGQVKYWITIDNPYVVAWHGY

ATGRLAPGIRGSPRLGYLVAHNLLLAHAKVWHLYNTSFRPTQGGQVSIAL

SSHWINPRRMDHSIKECQKSLDFVLGWFAKPIFIDGDYPESMKNNLSSLL

PDFTESEKKFIKGTADFFALSFGPTLSFQLLDPHMKFRQLESPSLRQLLS

WIDLEYNHPQIFIVENGWFVSGTTKRDDAKYMYYLKKFIMETLKAIKLDG

VDVIGYTAWSLMDGFEWHRGYSIRRGLFYVDFLSQEKTLLPKSSALFYQK

LIEKNGFPPLPENQPLEGTFPCDFAWGIVDNYIQVDTTLSQFTDLNVYLW

DVHHSKRLIKVDGVVTKKRKSYCVDFAAIQPQITLLQEMHVTHFRFSLDW

ALILPLGNQSQVNHTILQYYRCMVSELVRVNITPVVALWQPVAPNQGLPR

LLARQGAWENPYTALAFAEYARLCFQELGHHVKLWITMNEPYTRNMTYSA

GHNLLKAHALAWHVYNEKFRHAQNGKISIALQADWIEPACPFSQKDKEVA

ERVLEFDIGWLAEPIFGSGDYPWVMRDWLNQRNNFLLPYFTEDEKKLIQG

TFDFLALSHYTTILVDSEKEDPIKYNDYLEVQEMTDITWLNSPSQVAVVP

WGLRKVLNWLKFKYGDLPMYIISNGIDDGLHAEDDQLRVYYMQNYINEAL

KAHILDGINLCGYFAYSFNDRTAPRFGLYRFAADQFEPKPSMKHYRKIID

SNGFPGPETLEKFCPEEFTVCTECSFFHTRKPLVAFIAFLFFAFIVSLSL

IFYYSKKGRRRYQ

Monkey Klotho ECD (SEQ ID NO: 9)

MPASAPPRRPRPPPPSLSLSLLLVLLGLAGRRLRAEPGDGAQTWARFARP

PAPEAAGLFQGTFPDGFLWAVGSAAYQTEGGWQQHGKGASIWDTFTHHPL

APPGDSRIANVPSGAPSPLQPATGDVASDSYNNVFRDTEALRELGVTHYR

FSISWARVLPNGSAGVPNREGLRYYRRLLERLRELGVQPVVTLYHWDLPQ

RLQDAYGGWANRALADHFRDYAELCFRHFGGQVKYWITIDNPYVVAWHGY

ATGRLAPGIRGSPRLGYLVAHNLLLAHAKVWHLYNTSFRPTQGGQVSIAL

SSHWINPRRMTDHSIKECQKSLDFVLGWFAKPIFIDGDYPESMKNNLSSL

LPDFTESEKKFIKGTADFFALSFGPTLSFQLLDPHMKFRQLESPSLRQLL

SWIDLEYNHPQIFIVENGWFVSGTTKRDDAKYMYYLKKFIMETLKAIKLD

GVDVIGYTAWSLMDGFEWHRGYSIRRGLFYVDFLSQEKTLLPKSSALFYQ

KLIEKNGFPPLPENQPLEGTFPCDFAWGIVDNYIQVDTTLSQFTDLNVYL

WDVHHSKRLIKVDGVVTKKRKSYCVDFAAIQPQITLLQEMHVTHFRFSLD

WALILPLGNQSQVNHTILQYYRCMVSELVRVNITPVVALWQPVAPNQGLP

RLLARQGAWENPYTALAFAEYARLCFQELGHHVKLWITMNEPYTRNMTYS

AGHNLLKAHALAWHVYNEKFRHAQNGKISIALQADWIEPACPFSQKDKEV

AERVLEFDIGWLAEPIFGSGDYPWVMRDWLNQRNNFLLPYFTEDEKKLIQ

GTFDFLALSHYTTILVDSEKEDPIKYNDYLEVQEMTDITWLNSPSQVAVV

PWGLRKVLNWLKFKYGDLPMYIISNGIDDGLHAEDDQLRVYYMQNYINEA

-continued

LKAHILDGINLCGYFAYSFNDRTAPRFGLYRFAADQFEPKPSMKHYRKII
DSNGFPGPETLEKFCPEEFTVCTECSFFHTRKP

Mouse Klotho ECD - His tagged: 36-983
(SEQ ID NO: 10)
EPGQGAQTWARFARAPAPEAAGLLHDTFPDGFLWAVGSAAYQTEGGWRQH
GKGASIWDTFTHHSGAAPSDSPIVVAPSGAPSPPLSSTGDVASDSYNNVY
RDTEGLRELGVTHYRFSISWARVLPNGTAGTPNREGLRYYRRLLERLREL
GVQPVVTLYHWDLPQRLQDTYGGWANRALADHFRDYAELCFRHFGGQVKY
WITIDNPYVVAWHGYATGRLAPGVRGSSRLGYLVAHNLLLAHAKVWHLYN
TSFRPTQGGRVSIALSSHWINPRRMTDYNIRECQKSLDFVLGWFAKPIFI
DGDYPESMKNNLSSLLPDFTESEKRLIRGTADFFALSFGPTLSFQLLDPN
MKFRQLESPNLRQLLSWIDLEYNHPPIFIVENGWFVSGTTKRDDAKYMYY
LKKFIMETLKAIRLDGVDVIGYTAWSLMDGFEWHRGYSIRRGLFYVDFLS
QDKELLPKSSALFYQKLIEDNGFPPLPENQPLEGTFPCDFAWGVVDNYVQ
VDTTLSQFTDPNVYLWDVHHSKRLIKVDGVVAKKRKPYCVDFSAIRPQIT
LLREMRVTHFRFSLDWALILPLGNQTQVNHTVLHFYRCMISELVHANITP
VVALWQPAAPHQGLPHALAKHGAWENPHTALAFADYANLCFKELGHWVNL
WITMNEPNTRNMTYRAGHHLLRAHALAWHLYDDKFRAAQKGKISIALQAD
WIEPACPFSQNDKEVAERVLEFDIGWLAEPIFGSGDYPRVMRDWLNQKNN
FLLPYFTEDEKKLVRGSFDFLAVSHYTTILVDWEKEDPMKYNDYLEVQEM
TDITWLNSPSQVAVVPWGLRKVLNWLRFKYGDLPMYVTANGIDDDPHAEQ
DSLRIYYIKNYVNEALKAYVLDDINLCGYFAYSLSDRSAPKSGFYRYAAN
QFEPKPSMKHYRRIIDSNGFLGSGTLGRFCPEEYTVCTECGFFQTRKSHH
HHHH Mouse Klotho ECD
(SEQ ID NO: 11)
EPGQGAQTWARFARAPAPEAAGLLHDTFPDGFLWAVGSAAYQTEGGWRQH
GKGASIWDTFTHHSGAAPSDSPIVVAPSGAPSPPLSSTGDVASDSYNNVY
RDTEGLRELGVTHYRFSISWARVLPNGTAGTPNREGLRYYRRLLERLREL
GVQPVVTLYHWDLPQRLQDTYGGWANRALADHFRDYAELCFRHFGGQVKY
WITIDNPYVVAWHGYATGRLAPGVRGSSRLGYLVAHNLLLAHAKVWHLYN
TSFRPTQGGRVSIALSSHWINPRRMTDYNIRECQKSLDFVLGWFAKPIFI
DGDYPESMKNNLSSLLPDFTESEKRLIRGTADFFALSFGPTLSFQLLDPN
MKFRQLESPNLRQLLSWIDLEYNHPPIFIVENGWFVSGTTKRDDAKYMYY
LKKFIMETLKAIRLDGVDVIGYTAWSLMDGFEWHRGYSIRRGLFYVDFLS
QDKELLPKSSALFYQKLIEDNGFPPLPENQPLEGTFPCDFAWGVVDNYVQ
VDTTLSQFTDPNVYLWDVHHSKRLIKVDGVVAKKRKPYCVDFSAIRPQIT
LLREMRVTHFRFSLDWALILPLGNQTQVNHTVLHFYRCMISELVHANITP
VVALWQPAAPHQGLPHALAKHGAWENPHTALAFADYANLCFKELGHWVNL
WITMNEPNTRNMTYRAGHHLLRAHALAWHLYDDKFRAAQKGKISIALQAD
WIEPACPFSQNDKEVAERVLEFDIGWLAEPIFGSGDYPRVMRDWLNQKNN
FLLPYFTEDEKKLVRGSFDFLAVSHYTTILVDWEKEDPMKYNDYLEVQEM
TDITWLNSPSQVAVVPWGLRKVLNWLRFKYGDLPMYVTANGIDDDPHAEQ
DSLRIYYIKNYVNEALKAYVLDDINLCGYFAYSLSDRSAPKSGFYRYAAN
QFEPKPSMKHYRKIIDSNGFLGSGTLGRFCPEEYTVCTECGFFQTRKS

---

We claim:

1. A method of lowering serum phosphate levels in a patient, comprising administering an effective amount of soluble alpha-Klotho to the patient, wherein the soluble alpha-Klotho has the amino acid sequence of SEQ ID NO: 5.

2. A method of lowering serum calcium levels in a patient, comprising administering an effective amount of soluble alpha-Klotho to the patient, wherein the soluble alpha-Klotho has the amino acid sequence of SEQ ID NO: 5.

3. A method of increasing serum FGF23 levels in a patient, comprising administering an effective amount of soluble alpha-Klotho to the patient, wherein the soluble alpha-Klotho has the amino acid sequence of SEQ ID NO: 5.

* * * * *

SEQUENCE LISTING

```
<160> NUMBER OF SEQ ID NOS: 11

<210> SEQ ID NO 1
<211> LENGTH: 1014
<212> TYPE: PRT
<213> ORGANISM: Mus musculus

<400> SEQUENCE: 1

Met Leu Ala Arg Ala Pro Pro Arg Arg Pro Pro Arg Leu Val Leu Leu
1               5                   10                  15

Arg Leu Leu Leu Leu His Leu Leu Leu Leu Ala Leu Arg Ala Arg Cys
            20                  25                  30

Leu Ser Ala Glu Pro Gly Gln Gly Ala Gln Thr Trp Ala Arg Phe Ala
        35                  40                  45

Arg Ala Pro Ala Pro Glu Ala Ala Gly Leu Leu His Asp Thr Phe Pro
    50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
            100                 105                 110

Ser Gly Ala Pro Ser Pro Pro Leu Ser Ser Thr Gly Asp Val Ala Ser
```

-continued

```
            115                 120                 125
Asp Ser Tyr Asn Asn Val Tyr Arg Asp Thr Glu Gly Leu Arg Glu Leu
        130                 135                 140
Gly Val Thr His Tyr Arg Phe Ser Ile Ser Trp Ala Arg Val Leu Pro
145                 150                 155                 160
Asn Gly Thr Ala Gly Thr Pro Asn Arg Glu Gly Leu Arg Tyr Tyr Arg
                165                 170                 175
Arg Leu Leu Glu Arg Leu Arg Glu Leu Gly Val Gln Pro Val Val Thr
            180                 185                 190
Leu Tyr His Trp Asp Leu Pro Gln Arg Leu Gln Asp Thr Tyr Gly Gly
        195                 200                 205
Trp Ala Asn Arg Ala Leu Ala Asp His Phe Arg Asp Tyr Ala Glu Leu
210                 215                 220
Cys Phe Arg His Phe Gly Gly Gln Val Lys Tyr Trp Ile Thr Ile Asp
225                 230                 235                 240
Asn Pro Tyr Val Val Ala Trp His Gly Tyr Ala Thr Gly Arg Leu Ala
                245                 250                 255
Pro Gly Val Arg Gly Ser Ser Arg Leu Gly Tyr Leu Val Ala His Asn
            260                 265                 270
Leu Leu Leu Ala His Ala Lys Val Trp His Leu Tyr Asn Thr Ser Phe
        275                 280                 285
Arg Pro Thr Gln Gly Gly Arg Val Ser Ile Ala Leu Ser Ser His Trp
        290                 295                 300
Ile Asn Pro Arg Arg Met Thr Asp Tyr Asn Ile Arg Glu Cys Gln Lys
305                 310                 315                 320
Ser Leu Asp Phe Val Leu Gly Trp Phe Ala Lys Pro Ile Phe Ile Asp
                325                 330                 335
Gly Asp Tyr Pro Glu Ser Met Lys Asn Asn Leu Ser Ser Leu Leu Pro
            340                 345                 350
Asp Phe Thr Glu Ser Glu Lys Arg Leu Ile Arg Gly Thr Ala Asp Phe
        355                 360                 365
Phe Ala Leu Ser Phe Gly Pro Thr Leu Ser Phe Gln Leu Leu Asp Pro
        370                 375                 380
Asn Met Lys Phe Arg Gln Leu Glu Ser Pro Asn Leu Arg Gln Leu Leu
385                 390                 395                 400
Ser Trp Ile Asp Leu Glu Tyr Asn His Pro Pro Ile Phe Ile Val Glu
                405                 410                 415
Asn Gly Trp Phe Val Ser Gly Thr Thr Lys Arg Asp Asp Ala Lys Tyr
            420                 425                 430
Met Tyr Tyr Leu Lys Lys Phe Ile Met Glu Thr Leu Lys Ala Ile Arg
        435                 440                 445
Leu Asp Gly Val Asp Val Ile Gly Tyr Thr Ala Trp Ser Leu Met Asp
        450                 455                 460
Gly Phe Glu Trp His Arg Gly Tyr Ser Ile Arg Arg Gly Leu Phe Tyr
465                 470                 475                 480
Val Asp Phe Leu Ser Gln Asp Lys Glu Leu Leu Pro Lys Ser Ser Ala
                485                 490                 495
Leu Phe Tyr Gln Lys Leu Ile Glu Asp Asn Gly Phe Pro Pro Leu Pro
            500                 505                 510
Glu Asn Gln Pro Leu Glu Gly Thr Phe Pro Cys Asp Phe Ala Trp Gly
        515                 520                 525
Val Val Asp Asn Tyr Val Gln Val Asp Thr Thr Leu Ser Gln Phe Thr
        530                 535                 540
```

-continued

Asp Pro Asn Val Tyr Leu Trp Asp Val His His Ser Lys Arg Leu Ile
545                 550                 555                 560

Lys Val Asp Gly Val Ala Lys Lys Arg Lys Pro Tyr Cys Val Asp
            565                 570                 575

Phe Ser Ala Ile Arg Pro Gln Ile Thr Leu Leu Arg Glu Met Arg Val
        580                 585                 590

Thr His Phe Arg Phe Ser Leu Asp Trp Ala Leu Ile Leu Pro Leu Gly
            595                 600                 605

Asn Gln Thr Gln Val Asn His Thr Val Leu His Phe Tyr Arg Cys Met
        610                 615                 620

Ile Ser Glu Leu Val His Ala Asn Ile Thr Pro Val Val Ala Leu Trp
625                 630                 635                 640

Gln Pro Ala Ala Pro His Gln Gly Leu Pro His Ala Leu Ala Lys His
            645                 650                 655

Gly Ala Trp Glu Asn Pro His Thr Ala Leu Ala Phe Ala Asp Tyr Ala
            660                 665                 670

Asn Leu Cys Phe Lys Glu Leu Gly His Trp Val Asn Leu Trp Ile Thr
        675                 680                 685

Met Asn Glu Pro Asn Thr Arg Asn Met Thr Tyr Arg Ala Gly His His
690                 695                 700

Leu Leu Arg Ala His Ala Leu Ala Trp His Leu Tyr Asp Asp Lys Phe
705                 710                 715                 720

Arg Ala Ala Gln Lys Gly Lys Ile Ser Ile Ala Leu Gln Ala Asp Trp
            725                 730                 735

Ile Glu Pro Ala Cys Pro Phe Ser Gln Asn Asp Lys Glu Val Ala Glu
            740                 745                 750

Arg Val Leu Glu Phe Asp Ile Gly Trp Leu Ala Glu Pro Ile Phe Gly
        755                 760                 765

Ser Gly Asp Tyr Pro Arg Val Met Arg Asp Trp Leu Asn Gln Lys Asn
    770                 775                 780

Asn Phe Leu Leu Pro Tyr Phe Thr Glu Asp Glu Lys Lys Leu Val Arg
785                 790                 795                 800

Gly Ser Phe Asp Phe Leu Ala Val Ser His Tyr Thr Thr Ile Leu Val
            805                 810                 815

Asp Trp Glu Lys Glu Asp Pro Met Lys Tyr Asn Asp Tyr Leu Glu Val
        820                 825                 830

Gln Glu Met Thr Asp Ile Thr Trp Leu Asn Ser Pro Ser Gln Val Ala
        835                 840                 845

Val Val Pro Trp Gly Leu Arg Lys Val Leu Asn Trp Leu Arg Phe Lys
    850                 855                 860

Tyr Gly Asp Leu Pro Met Tyr Val Thr Ala Asn Gly Ile Asp Asp Asp
865                 870                 875                 880

Pro His Ala Glu Gln Asp Ser Leu Arg Ile Tyr Tyr Ile Lys Asn Tyr
            885                 890                 895

Val Asn Glu Ala Leu Lys Ala Tyr Val Leu Asp Asp Ile Asn Leu Cys
        900                 905                 910

Gly Tyr Phe Ala Tyr Ser Leu Ser Asp Arg Ser Ala Pro Lys Ser Gly
            915                 920                 925

Phe Tyr Arg Tyr Ala Ala Asn Gln Phe Glu Pro Lys Pro Ser Met Lys
        930                 935                 940

His Tyr Arg Arg Ile Ile Asp Ser Asn Gly Phe Leu Gly Ser Gly Thr
945                 950                 955                 960

-continued

Leu Gly Arg Phe Cys Pro Glu Glu Tyr Thr Val Cys Thr Glu Cys Gly
                965                 970                 975

Phe Phe Gln Thr Arg Lys Ser Leu Leu Val Phe Ile Ser Phe Leu Val
                980                 985                 990

Phe Thr Phe Ile Ile Ser Leu Ala Leu Ile Phe His Tyr Ser Lys Lys
                995                1000                1005

Gly Gln Arg Ser Tyr Lys
       1010

<210> SEQ ID NO 2
<211> LENGTH: 966
<212> TYPE: PRT
<213> ORGANISM: Artificial Sequence
<220> FEATURE:
<223> OTHER INFORMATION: Synthetic Construct

<400> SEQUENCE: 2

Met Pro Leu Leu Leu Leu Pro Leu Leu Trp Ala Gly Ala Leu Ala
1               5                   10                  15

Met Ala Glu Pro Gly Gln Gly Ala Gln Thr Trp Ala Arg Phe Ala Arg
                20                  25                  30

Ala Pro Ala Pro Glu Ala Ala Gly Leu Leu His Asp Thr Phe Pro Asp
                35                  40                  45

Gly Phe Leu Trp Ala Val Gly Ser Ala Ala Tyr Gln Thr Glu Gly Gly
        50                  55                  60

Trp Arg Gln His Gly Lys Gly Ala Ser Ile Trp Asp Thr Phe Thr His
65              70                  75                  80

His Ser Gly Ala Ala Pro Ser Asp Ser Pro Ile Val Val Ala Pro Ser
                85                  90                  95

Gly Ala Pro Ser Pro Leu Ser Ser Thr Gly Asp Val Ala Ser Asp
                100                 105                 110

Ser Tyr Asn Asn Val Tyr Arg Asp Thr Glu Gly Leu Arg Glu Leu Gly
                115                 120                 125

Val Thr His Tyr Arg Phe Ser Ile Ser Trp Ala Arg Val Leu Pro Asn
        130                 135                 140

Gly Thr Ala Gly Thr Pro Asn Arg Glu Gly Leu Arg Tyr Tyr Arg Arg
145                 150                 155                 160

Leu Leu Glu Arg Leu Arg Glu Leu Gly Val Gln Pro Val Val Thr Leu
                165                 170                 175

Tyr His Trp Asp Leu Pro Gln Arg Leu Gln Asp Thr Tyr Gly Gly Trp
                180                 185                 190

Ala Asn Arg Ala Leu Ala Asp His Phe Arg Asp Tyr Ala Glu Leu Cys
                195                 200                 205

Phe Arg His Phe Gly Gly Gln Val Lys Tyr Trp Ile Thr Ile Asp Asn
        210                 215                 220

Pro Tyr Val Val Ala Trp His Gly Tyr Ala Thr Gly Arg Leu Ala Pro
225                 230                 235                 240

Gly Val Arg Gly Ser Ser Arg Leu Gly Tyr Leu Val Ala His Asn Leu
                245                 250                 255

Leu Leu Ala His Ala Lys Val Trp His Leu Tyr Asn Thr Ser Phe Arg
                260                 265                 270

Pro Thr Gln Gly Gly Arg Val Ser Ile Ala Leu Ser Ser His Trp Ile
        275                 280                 285

Asn Pro Arg Arg Met Thr Asp Tyr Asn Ile Arg Glu Cys Gln Lys Ser
        290                 295                 300

```
Leu Asp Phe Val Leu Gly Trp Phe Ala Lys Pro Ile Phe Ile Asp Gly
305                 310                 315                 320

Asp Tyr Pro Glu Ser Met Lys Asn Asn Leu Ser Ser Leu Leu Pro Asp
            325                 330                 335

Phe Thr Glu Ser Glu Lys Arg Leu Ile Arg Gly Thr Ala Asp Phe Phe
        340                 345                 350

Ala Leu Ser Phe Gly Pro Thr Leu Ser Phe Gln Leu Leu Asp Pro Asn
        355                 360                 365

Met Lys Phe Arg Gln Leu Glu Ser Pro Asn Leu Arg Gln Leu Leu Ser
370                 375                 380

Trp Ile Asp Leu Glu Tyr Asn His Pro Pro Ile Phe Ile Val Glu Asn
385                 390                 395                 400

Gly Trp Phe Val Ser Gly Thr Thr Lys Arg Asp Asp Ala Lys Tyr Met
                405                 410                 415

Tyr Tyr Leu Lys Lys Phe Ile Met Glu Thr Leu Lys Ala Ile Arg Leu
            420                 425                 430

Asp Gly Val Asp Val Ile Gly Tyr Thr Ala Trp Ser Leu Met Asp Gly
        435                 440                 445

Phe Glu Trp His Arg Gly Tyr Ser Ile Arg Arg Gly Leu Phe Tyr Val
450                 455                 460

Asp Phe Leu Ser Gln Asp Lys Glu Leu Leu Pro Lys Ser Ser Ala Leu
465                 470                 475                 480

Phe Tyr Gln Lys Leu Ile Glu Asp Asn Gly Phe Pro Pro Leu Pro Glu
            485                 490                 495

Asn Gln Pro Leu Glu Gly Thr Phe Pro Cys Asp Phe Ala Trp Gly Val
        500                 505                 510

Val Asp Asn Tyr Val Gln Val Asp Thr Thr Leu Ser Gln Phe Thr Asp
515                 520                 525

Pro Asn Val Tyr Leu Trp Asp Val His His Ser Lys Arg Leu Ile Lys
    530                 535                 540

Val Asp Gly Val Val Ala Lys Lys Arg Lys Pro Tyr Cys Val Asp Phe
545                 550                 555                 560

Ser Ala Ile Arg Pro Gln Ile Thr Leu Leu Arg Glu Met Arg Val Thr
            565                 570                 575

His Phe Arg Phe Ser Leu Asp Trp Ala Leu Ile Leu Pro Leu Gly Asn
        580                 585                 590

Gln Thr Gln Val Asn His Thr Val Leu His Phe Tyr Arg Cys Met Ile
    595                 600                 605

Ser Glu Leu Val His Ala Asn Ile Thr Pro Val Val Ala Leu Trp Gln
    610                 615                 620

Pro Ala Ala Pro His Gln Gly Leu Pro His Ala Leu Ala Lys His Gly
625                 630                 635                 640

Ala Trp Glu Asn Pro His Thr Ala Leu Ala Phe Ala Asp Tyr Ala Asn
            645                 650                 655

Leu Cys Phe Lys Glu Leu Gly His Trp Val Asn Leu Trp Ile Thr Met
        660                 665                 670

Asn Glu Pro Asn Thr Arg Asn Met Thr Tyr Arg Ala Gly His His Leu
    675                 680                 685

Leu Arg Ala His Ala Leu Ala Trp His Leu Tyr Asp Asp Lys Phe Arg
        690                 695                 700

Ala Ala Gln Lys Gly Lys Ile Ser Ile Ala Leu Gln Ala Asp Trp Ile
705                 710                 715                 720

Glu Pro Ala Cys Pro Phe Ser Gln Asn Asp Lys Glu Val Ala Glu Arg
```

```
            725                 730                 735
Val Leu Glu Phe Asp Ile Gly Trp Leu Ala Glu Pro Ile Phe Gly Ser
            740                 745                 750
Gly Asp Tyr Pro Arg Val Met Arg Asp Trp Leu Asn Gln Lys Asn Asn
            755                 760                 765
Phe Leu Leu Pro Tyr Phe Thr Glu Asp Glu Lys Lys Leu Val Arg Gly
            770                 775                 780
Ser Phe Asp Phe Leu Ala Val Ser His Tyr Thr Thr Ile Leu Val Asp
785                 790                 795                 800
Trp Glu Lys Glu Asp Pro Met Lys Tyr Asn Asp Tyr Leu Glu Val Gln
            805                 810                 815
Glu Met Thr Asp Ile Thr Trp Leu Asn Ser Pro Ser Gln Val Ala Val
            820                 825                 830
Val Pro Trp Gly Leu Arg Lys Val Leu Asn Trp Leu Arg Phe Lys Tyr
            835                 840                 845
Gly Asp Leu Pro Met Tyr Val Thr Ala Asn Gly Ile Asp Asp Asp Pro
            850                 855                 860
His Ala Glu Gln Asp Ser Leu Arg Ile Tyr Tyr Ile Lys Asn Tyr Val
865                 870                 875                 880
Asn Glu Ala Leu Lys Ala Tyr Val Leu Asp Asp Ile Asn Leu Cys Gly
            885                 890                 895
Tyr Phe Ala Tyr Ser Leu Ser Asp Arg Ser Ala Pro Lys Ser Gly Phe
            900                 905                 910
Tyr Arg Tyr Ala Ala Asn Gln Phe Glu Pro Lys Pro Ser Met Lys His
            915                 920                 925
Tyr Arg Lys Ile Ile Asp Ser Asn Gly Phe Leu Gly Ser Gly Thr Leu
            930                 935                 940
Gly Arg Phe Cys Pro Glu Tyr Thr Val Cys Thr Glu Cys Gly Phe
945                 950                 955                 960
Phe Gln Thr Arg Lys Ser
            965

<210> SEQ ID NO 3
<211> LENGTH: 1023
<212> TYPE: PRT
<213> ORGANISM: Artificial Sequence
<220> FEATURE:
<223> OTHER INFORMATION: Synthetic Construct

<400> SEQUENCE: 3

Met Thr Met Ile Thr Asp Ser Leu Ala Val Val Leu Gln Arg Arg Asp
1               5                   10                  15
Trp Glu Asn Pro Gly Val Thr Gln Leu Asn Arg Leu Ala Ala His Pro
            20                  25                  30
Pro Phe Ala Ser Trp Arg Asn Ser Glu Glu Ala Arg Thr Asp Arg Pro
            35                  40                  45
Ser Gln Gln Leu Arg Ser Leu Asn Gly Glu Trp Arg Phe Ala Trp Phe
        50                  55                  60
Pro Ala Pro Glu Ala Val Pro Glu Ser Trp Leu Glu Cys Asp Leu Pro
65                  70                  75                  80
Glu Ala Asp Thr Val Val Val Pro Ser Asn Trp Gln Met His Gly Tyr
                85                  90                  95
Asp Ala Pro Ile Tyr Thr Asn Val Thr Tyr Pro Ile Thr Val Asn Pro
            100                 105                 110
Pro Phe Val Pro Thr Glu Asn Pro Thr Gly Cys Tyr Ser Leu Thr Phe
```

-continued

```
            115                 120                 125
Asn Val Asp Glu Ser Trp Leu Gln Glu Gly Gln Thr Arg Ile Ile Phe
130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                    165                 170                 175

Phe Leu Arg Ala Gly Glu Asn Arg Leu Ala Val Met Val Leu Trp Ser
                180                 185                 190

Asp Gly Ser Tyr Leu Glu Asp Gln Asp Met Trp Arg Met Ser Gly Ile
            195                 200                 205

Phe Arg Asp Val Ser Leu Leu His Lys Pro Thr Thr Gln Ile Ser Asp
210                 215                 220

Phe His Val Ala Thr Arg Phe Asn Asp Asp Phe Ser Arg Ala Val Leu
225                 230                 235                 240

Glu Ala Glu Val Gln Met Cys Gly Glu Leu Arg Asp Tyr Leu Arg Val
                    245                 250                 255

Thr Val Ser Leu Trp Gln Gly Glu Thr Gln Val Ala Ser Gly Thr Ala
                260                 265                 270

Pro Phe Gly Gly Glu Ile Ile Asp Glu Arg Gly Gly Tyr Ala Asp Arg
            275                 280                 285

Val Thr Leu Arg Leu Asn Val Glu Asn Pro Lys Leu Trp Ser Ala Glu
290                 295                 300

Ile Pro Asn Leu Tyr Arg Ala Val Val Glu Leu His Thr Ala Asp Gly
305                 310                 315                 320

Thr Leu Ile Glu Ala Glu Ala Cys Asp Val Gly Phe Arg Glu Val Arg
                    325                 330                 335

Ile Glu Asn Gly Leu Leu Leu Leu Asn Gly Lys Pro Leu Leu Ile Arg
                340                 345                 350

Gly Val Asn Arg His Glu His His Pro Leu His Gly Gln Val Met Asp
            355                 360                 365

Glu Gln Thr Met Val Gln Asp Ile Leu Leu Met Lys Gln Asn Asn Phe
370                 375                 380

Asn Ala Val Arg Cys Ser His Tyr Pro Asn His Pro Leu Trp Tyr Thr
385                 390                 395                 400

Leu Cys Asp Arg Tyr Gly Leu Tyr Val Val Asp Glu Ala Asn Ile Glu
                    405                 410                 415

Thr His Gly Met Val Pro Met Asn Arg Leu Thr Asp Asp Pro Arg Trp
                420                 425                 430

Leu Pro Ala Met Ser Glu Arg Val Thr Arg Met Val Gln Arg Asp Arg
            435                 440                 445

Asn His Pro Ser Val Ile Ile Trp Ser Leu Gly Asn Glu Ser Gly His
450                 455                 460

Gly Ala Asn His Asp Ala Leu Tyr Arg Trp Ile Lys Ser Val Asp Pro
465                 470                 475                 480

Ser Arg Pro Val Gln Tyr Glu Gly Gly Gly Ala Asp Thr Thr Ala Thr
                    485                 490                 495

Asp Ile Ile Cys Pro Met Tyr Ala Arg Val Asp Glu Asp Gln Pro Phe
                500                 505                 510

Pro Ala Val Pro Lys Trp Ser Ile Lys Lys Trp Leu Ser Leu Pro Gly
            515                 520                 525

Glu Thr Arg Pro Leu Ile Leu Cys Glu Tyr Ala His Ala Met Gly Asn
530                 535                 540
```

```
Ser Leu Gly Gly Phe Ala Lys Tyr Trp Gln Ala Phe Arg Gln Tyr Pro
545                 550                 555                 560

Arg Leu Gln Gly Gly Phe Val Trp Asp Trp Val Asp Gln Ser Leu Ile
            565                 570                 575

Lys Tyr Asp Glu Asn Gly Asn Pro Trp Ser Ala Tyr Gly Gly Asp Phe
        580                 585                 590

Gly Asp Thr Pro Asn Asp Arg Gln Phe Cys Met Asn Gly Leu Val Phe
            595                 600                 605

Ala Asp Arg Thr Pro His Pro Ala Leu Thr Glu Ala Lys His Gln Gln
610                 615                 620

Gln Phe Phe Gln Phe Arg Leu Ser Gly Gln Thr Ile Glu Val Thr Ser
625                 630                 635                 640

Glu Tyr Leu Phe Arg His Ser Asp Asn Glu Leu Leu His Trp Met Val
                645                 650                 655

Ala Leu Asp Gly Lys Pro Leu Ala Ser Gly Glu Val Pro Leu Asp Val
            660                 665                 670

Ala Pro Gln Gly Lys Gln Leu Ile Glu Leu Pro Glu Leu Pro Gln Pro
            675                 680                 685

Glu Ser Ala Gly Gln Leu Trp Leu Thr Val Arg Val Val Gln Pro Asn
690                 695                 700

Ala Thr Ala Trp Ser Glu Ala Gly His Ile Ser Ala Trp Gln Gln Trp
705                 710                 715                 720

Arg Leu Ala Glu Asn Leu Ser Val Thr Leu Pro Ala Ala Ser His Ala
            725                 730                 735

Ile Pro His Leu Thr Thr Ser Glu Met Asp Phe Cys Ile Glu Leu Gly
            740                 745                 750

Asn Lys Arg Trp Gln Phe Asn Arg Gln Ser Gly Phe Leu Ser Gln Met
        755                 760                 765

Trp Ile Gly Asp Lys Lys Gln Leu Leu Thr Pro Leu Arg Asp Gln Phe
770                 775                 780

Thr Arg Ala Pro Leu Asp Asn Asp Ile Gly Val Ser Glu Ala Thr Arg
785                 790                 795                 800

Ile Asp Pro Asn Ala Trp Val Glu Arg Trp Lys Ala Ala Gly His Tyr
                805                 810                 815

Gln Ala Glu Ala Ala Leu Leu Gln Cys Thr Ala Asp Thr Leu Ala Asp
            820                 825                 830

Ala Val Leu Ile Thr Thr Ala His Ala Trp Gln His Gln Gly Lys Thr
            835                 840                 845

Leu Phe Ile Ser Arg Lys Thr Tyr Arg Ile Asp Gly Ser Gly Gln Met
    850                 855                 860

Ala Ile Thr Val Asp Val Glu Val Ala Ser Asp Thr Pro His Pro Ala
865                 870                 875                 880

Arg Ile Gly Leu Asn Cys Gln Leu Ala Gln Val Ala Glu Arg Val Asn
                885                 890                 895

Trp Leu Gly Leu Gly Pro Gln Glu Asn Tyr Pro Asp Arg Leu Thr Ala
            900                 905                 910

Ala Cys Phe Asp Arg Trp Asp Leu Pro Leu Ser Asp Met Tyr Thr Pro
        915                 920                 925

Tyr Val Phe Pro Ser Glu Asn Gly Leu Arg Cys Gly Thr Arg Glu Leu
        930                 935                 940

Asn Tyr Gly Pro His Gln Trp Arg Gly Asp Phe Gln Phe Asn Ile Ser
945                 950                 955                 960
```

```
Arg Tyr Ser Gln Gln Gln Leu Met Glu Thr Ser His Arg His Leu Leu
                965                 970                 975

His Ala Glu Glu Gly Thr Trp Leu Asn Ile Asp Gly Phe His Met Gly
            980                 985                 990

Ile Gly Gly Asp Asp Ser Trp Ser Pro Ser Val Ser Ala Glu Phe Gln
        995                1000                1005

Leu Ser Ala Gly Arg Tyr His Tyr Gln Leu Val Trp Cys Gln Lys
   1010                1015                1020

<210> SEQ ID NO 4
<211> LENGTH: 1010
<212> TYPE: PRT
<213> ORGANISM: Homo sapiens

<400> SEQUENCE: 4

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Val Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His Pro
                85                  90                  95

Leu Ala Pro Pro Gly Asp Ser Arg Asn Ala Ser Leu Pro Leu Gly Ala
            100                 105                 110

Pro Ser Pro Leu Gln Pro Ala Thr Gly Asp Val Ala Ser Asp Ser Tyr
        115                 120                 125

Asn Asn Val Phe Arg Asp Thr Glu Ala Leu Arg Glu Leu Gly Val Thr
    130                 135                 140

His Tyr Arg Phe Ser Ile Ser Trp Ala Arg Val Leu Pro Asn Gly Ser
145                 150                 155                 160

Ala Gly Val Pro Asn Arg Glu Gly Leu Arg Tyr Tyr Arg Arg Leu Leu
                165                 170                 175

Glu Arg Leu Arg Glu Leu Gly Val Gln Pro Val Val Thr Leu Tyr His
            180                 185                 190

Trp Leu Pro Gln Arg Leu Gln Asp Ala Tyr Gly Gly Trp Ala Asn Arg
        195                 200                 205

Ala Leu Ala Asp His Phe Arg Asp Tyr Ala Glu Leu Cys Phe Arg His
    210                 215                 220

Phe Gly Gly Gln Val Lys Tyr Trp Ile Thr Ile Asp Asn Pro Tyr Val
225                 230                 235                 240

Val Ala Trp His Gly Tyr Ala Thr Gly Arg Leu Ala Pro Gly Ile Arg
                245                 250                 255

Gly Ser Pro Arg Leu Gly Tyr Leu Val Ala His Asn Leu Leu Leu Ala
            260                 265                 270

His Ala Lys Val Trp His Leu Tyr Asn Thr Ser Phe Arg Pro Thr Gln
        275                 280                 285

Gly Gly Gln Val Ser Ile Ala Leu Ser Ser His Trp Ile Asn Pro Arg
    290                 295                 300

Arg Met Thr Asp His Ser Ile Lys Glu Cys Gln Lys Ser Leu Asp Phe
305                 310                 315                 320
```

```
Val Leu Gly Trp Phe Ala Lys Pro Val Phe Ile Asp Gly Asp Tyr Pro
                325                 330                 335

Glu Ser Met Lys Asn Asn Leu Ser Ser Ile Leu Pro Asp Phe Thr Glu
                340                 345                 350

Ser Glu Lys Lys Phe Ile Lys Gly Thr Ala Asp Phe Phe Ala Leu Cys
                355                 360                 365

Phe Gly Pro Thr Leu Ser Phe Gln Leu Leu Asp Pro His Met Lys Phe
                370                 375                 380

Arg Gln Leu Glu Ser Pro Asn Leu Arg Gln Leu Leu Ser Trp Ile Asp
385                 390                 395                 400

Leu Glu Phe Asn His Pro Gln Ile Phe Ile Val Glu Asn Gly Trp Phe
                405                 410                 415

Val Ser Gly Thr Thr Lys Arg Asp Asp Ala Lys Tyr Met Tyr Tyr Leu
                420                 425                 430

Lys Lys Phe Ile Met Glu Thr Leu Lys Ala Ile Lys Leu Asp Gly Val
                435                 440                 445

Asp Val Ile Gly Tyr Thr Ala Trp Ser Leu Met Asp Gly Phe Glu Trp
            450                 455                 460

His Arg Gly Tyr Ser Ile Arg Arg Gly Leu Phe Tyr Val Asp Phe Leu
465                 470                 475                 480

Ser Gln Asp Lys Met Leu Leu Pro Lys Ser Ser Ala Leu Phe Tyr Gln
                485                 490                 495

Lys Leu Ile Glu Lys Asn Gly Phe Pro Pro Leu Pro Glu Asn Gln Pro
                500                 505                 510

Leu Glu Gly Thr Phe Pro Cys Asp Phe Ala Trp Gly Val Val Asp Asn
                515                 520                 525

Tyr Ile Gln Val Asp Thr Thr Leu Ser Gln Phe Thr Asp Leu Asn Val
            530                 535                 540

Tyr Leu Trp Asp Val His His Ser Lys Arg Leu Ile Lys Val Asp Gly
545                 550                 555                 560

Val Val Thr Lys Lys Arg Lys Ser Tyr Cys Val Asp Phe Ala Ala Ile
                565                 570                 575

Gln Pro Gln Ile Ala Leu Leu Gln Glu Met His Val Thr His Phe Arg
                580                 585                 590

Phe Ser Leu Asp Trp Ala Leu Ile Leu Pro Leu Gly Asn Gln Ser Gln
                595                 600                 605

Val Asn His Thr Ile Leu Gln Tyr Tyr Arg Cys Met Ala Ser Glu Leu
            610                 615                 620

Val Arg Val Asn Ile Thr Pro Val Val Ala Leu Trp Gln Pro Met Ala
625                 630                 635                 640

Pro Asn Gln Gly Leu Pro Arg Leu Leu Ala Arg Gln Gly Ala Trp Glu
                645                 650                 655

Asn Pro Tyr Thr Ala Leu Ala Phe Ala Glu Tyr Ala Arg Leu Cys Phe
                660                 665                 670

Gln Glu Leu Gly His His Val Lys Leu Trp Ile Thr Met Asn Glu Pro
                675                 680                 685

Tyr Thr Arg Asn Met Thr Tyr Ser Ala Gly His Asn Leu Leu Lys Ala
            690                 695                 700

His Ala Leu Ala Trp His Val Tyr Asn Glu Lys Phe Arg His Ala Gln
705                 710                 715                 720

Asn Gly Lys Ile Ser Ile Ala Leu Gln Ala Asp Trp Ile Glu Pro Ala
                725                 730                 735
```

```
Cys Pro Phe Ser Gln Lys Asp Lys Glu Val Ala Glu Arg Val Leu Glu
                740                 745                 750

Phe Asp Ile Gly Trp Leu Ala Glu Pro Ile Phe Gly Ser Gly Asp Tyr
            755                 760                 765

Pro Trp Val Met Arg Asp Trp Leu Asn Gln Arg Asn Asn Phe Leu Leu
770                 775                 780

Pro Tyr Phe Thr Glu Asp Glu Lys Lys Leu Ile Gln Gly Thr Phe Asp
785                 790                 795                 800

Phe Leu Ala Leu Ser His Tyr Thr Thr Ile Leu Val Asp Ser Glu Lys
                805                 810                 815

Glu Asp Pro Ile Lys Tyr Asn Asp Tyr Leu Glu Val Gln Glu Met Thr
            820                 825                 830

Asp Ile Thr Trp Leu Asn Ser Pro Ser Gln Val Ala Val Pro Trp
        835                 840                 845

Gly Leu Arg Lys Val Leu Asn Trp Leu Lys Phe Lys Tyr Gly Asp Leu
            850                 855                 860

Pro Met Tyr Ile Ile Ser Asn Gly Ile Asp Asp Gly Leu His Ala Glu
865                 870                 875                 880

Asp Asp Gln Leu Arg Val Tyr Tyr Met Gln Asn Tyr Ile Asn Glu Ala
                885                 890                 895

Leu Lys Ala His Ile Leu Asp Gly Ile Asn Leu Cys Gly Tyr Phe Ala
            900                 905                 910

Tyr Ser Phe Asn Asp Arg Thr Ala Pro Arg Phe Gly Leu Tyr Arg Tyr
        915                 920                 925

Ala Ala Asp Gln Phe Glu Pro Lys Ala Ser Met Lys His Tyr Arg Lys
            930                 935                 940

Ile Ile Asp Ser Asn Gly Phe Pro Gly Pro Glu Thr Leu Glu Arg Phe
945                 950                 955                 960

Cys Pro Glu Glu Phe Thr Val Cys Thr Glu Cys Ser Phe Phe His Thr
                965                 970                 975

Arg Lys Ser Leu Leu Ala Phe Ile Ala Phe Leu Phe Ala Ser Ile
            980                 985                 990

Ile Ser Leu Ser Leu Ile Phe Tyr Tyr Ser Lys Lys Gly Arg Arg Ser
        995                 1000                1005

Tyr Lys
   1010

<210> SEQ ID NO 5
<211> LENGTH: 981
<212> TYPE: PRT
<213> ORGANISM: Homo sapiens

<400> SEQUENCE: 5

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Val Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95
```

```
Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510
```

-continued

```
Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
```

```
                930             935             940
Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser
            980

<210> SEQ ID NO 6
<211> LENGTH: 1014
<212> TYPE: PRT
<213> ORGANISM: Rattus rattus

<400> SEQUENCE: 6

Met Pro Ala Arg Ala Pro Pro Arg Arg Leu Pro Arg Leu Leu Leu Leu
1               5                   10                  15

Arg Leu Leu Ser Leu His Leu Leu Leu Thr Leu Arg Ala Arg Cys
                20                  25                  30

Leu Ser Ala Glu Pro Gly Gln Gly Ala Gln Thr Trp Ala Arg Phe Ala
            35                  40                  45

Arg Pro Pro Val Pro Glu Ala Ser Gly Leu Leu His Asp Thr Phe Pro
        50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Pro Arg Ala Ile Pro Glu Asp Ser Pro Ile Val Met Ala Pro
            100                 105                 110

Ser Gly Ala Pro Leu Pro Pro Leu Pro Ser Thr Gly Asp Val Ala Ser
        115                 120                 125

Asp Ser Tyr Asn Asn Val Tyr Arg Asp Thr Glu Gly Leu Arg Glu Leu
130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Thr Tyr Gly Gly
        195                 200                 205

Trp Ala Asn Arg Ala Leu Ala Asp His Phe Arg Asp Tyr Ala Glu Leu
210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
            260                 265                 270

Leu Leu Leu Ala His Ala Lys Val Trp Arg Leu Tyr Asn Thr Ser Phe
        275                 280                 285

Arg Pro Thr Gln Gly Gly Arg Val Ser Ile Ala Leu Gly Ser His Trp
        290                 295                 300

Ile Thr Pro Arg Arg Met Thr Asp Tyr His Ile Arg Glu Cys Gln Lys
305                 310                 315                 320
```

```
Ser Leu Asp Phe Val Leu Gly Trp Phe Ala Lys Pro Ile Phe Ile Asp
            325                 330                 335

Gly Asp Tyr Pro Lys Ser Met Lys Asn Asn Leu Ser Ser Leu Leu Pro
        340                 345                 350

Asp Phe Thr Glu Ser Glu Lys Arg Phe Ile Arg Gly Thr Ala Asp Phe
    355                 360                 365

Phe Ala Leu Ser Phe Gly Pro Thr Leu Ser Phe Gln Leu Leu Asp Pro
370                 375                 380

Ser Met Lys Phe Arg Gln Leu Glu Ser Pro Ser Leu Arg Gln Leu Leu
385                 390                 395                 400

Ser Trp Ile Asp Leu Glu Tyr Asn His Pro Gln Ile Phe Ile Val Glu
                405                 410                 415

Asn Gly Trp Phe Val Ser Gly Thr Thr Arg Arg Asp Asp Ala Lys Tyr
            420                 425                 430

Met Tyr Tyr Leu Lys Lys Phe Ile Met Glu Ser Leu Lys Ala Ile Arg
        435                 440                 445

Leu Asp Gly Val Asp Val Ile Gly Tyr Thr Ala Trp Ser Leu Met Asp
    450                 455                 460

Gly Phe Glu Trp His Arg Gly Tyr Ser Ile Arg Arg Gly Leu Phe Tyr
465                 470                 475                 480

Val Asp Phe Leu Ser Gln Asp Lys Glu Leu Leu Pro Lys Ser Ser Ala
                485                 490                 495

Leu Phe Tyr Gln Lys Leu Ile Glu Asn Asn Gly Phe Pro Pro Leu Pro
            500                 505                 510

Glu Asn Gln Pro Leu Glu Gly Thr Phe Pro Cys Asp Phe Ala Trp Gly
        515                 520                 525

Val Val Asp Asn Tyr Ile Gln Val Asp Pro Thr Leu Ser Gln Phe Thr
    530                 535                 540

Asp Pro Asn Val Tyr Leu Trp Asp Val His His Ser Lys Arg Leu Ile
545                 550                 555                 560

Lys Val Asp Gly Val Val Ala Lys Lys Arg Lys Pro Tyr Cys Val Asp
                565                 570                 575

Phe Ser Ala Ile Arg Pro Gln Ile Thr Leu Leu Arg Glu Met Arg Val
            580                 585                 590

Thr His Phe Arg Phe Ser Leu Asp Trp Ala Leu Ile Leu Pro Leu Gly
        595                 600                 605

Asn Gln Thr Gln Val Asn Arg Thr Val Leu His Phe Tyr Arg Cys Met
    610                 615                 620

Val Ser Glu Leu Val His Ala Asn Ile Thr Pro Val Val Ala Leu Trp
625                 630                 635                 640

Gln Pro Ala Thr Pro His Gln Gly Leu Pro His Ala Leu Ala Lys His
                645                 650                 655

Gly Ala Trp Glu Asn Pro His Thr Ala Leu Ala Phe Ala Asp Tyr Ala
            660                 665                 670

Asn Leu Cys Phe Glu Leu Gly His Trp Val Lys Phe Trp Ile Thr
        675                 680                 685

Ile Asn Glu Pro Asn Ser Arg Asn Met Thr Tyr Arg Ala Gly His His
    690                 695                 700

Leu Leu Lys Ala His Ala Leu Ala Trp His Leu Tyr Asp Asp Lys Phe
705                 710                 715                 720

Arg Ala Ala Gln Lys Gly Lys Ile Ser Ile Ala Leu Gln Val Asp Trp
                725                 730                 735

Ile Glu Pro Ala Cys Pro Phe Ser Gln Lys Asp Lys Glu Val Ala Glu
```

```
                740             745             750
Arg Val Leu Glu Phe Asp Val Gly Trp Leu Ala Glu Pro Ile Phe Gly
            755             760             765

Ser Gly Asp Tyr Pro His Val Met Arg Glu Trp Leu Asn Gln Lys Asn
        770             775             780

Asn Phe Leu Leu Pro Tyr Phe Thr Glu Asp Lys Lys Leu Ile Arg
785             790             795             800

Gly Ser Phe Asp Phe Leu Ala Leu Ser His Tyr Thr Thr Ile Leu Val
                805             810             815

Asp Trp Glu Lys Glu Asp Pro Ile Lys Tyr Asn Asp Tyr Leu Glu Val
            820             825             830

Gln Glu Met Thr Asp Ile Thr Trp Leu Asn Ser Pro Asn Gln Val Ala
        835             840             845

Val Val Pro Trp Gly Leu Arg Lys Ala Leu Asn Trp Leu Arg Phe Lys
    850             855             860

Tyr Gly Asp Leu Pro Met Phe Val Thr Ala Asn Gly Ile Asp Asp
865             870             875             880

Pro His Ala Glu Gln Asp Ser Leu Arg Met Tyr Tyr Ile Lys Asn Tyr
                885             890             895

Val Asn Glu Ala Leu Lys Ala Tyr Val Leu Asp Gly Ile Asn Leu Cys
            900             905             910

Gly Tyr Phe Ala Tyr Ser Leu Ser Asp Arg Ser Val Pro Lys Ser Gly
        915             920             925

Phe Tyr Arg Tyr Ala Ala Asn Gln Phe Glu Pro Lys Pro Ser Ile Lys
    930             935             940

His Tyr Arg Lys Ile Ile Asp Asn Asn Gly Phe Leu Gly Ser Gly Thr
945             950             955             960

Leu Gly Arg Phe Cys Pro Glu Glu Tyr Thr Val Cys Thr Gly Cys Gly
                965             970             975

Phe Phe Gln Thr Arg Lys Ser Leu Leu Ala Phe Ile Ser Phe Leu Val
            980             985             990

Phe Ala Phe Val Thr Ser Leu Ala Leu Ile Tyr Tyr Tyr Ser Lys Lys
        995             1000            1005

Gly Arg Arg Arg Tyr Lys
    1010

<210> SEQ ID NO 7
<211> LENGTH: 983
<212> TYPE: PRT
<213> ORGANISM: Rattus rattus

<400> SEQUENCE: 7

Met Pro Ala Arg Ala Pro Pro Arg Arg Leu Pro Arg Leu Leu Leu Leu
1               5               10              15

Arg Leu Leu Ser Leu His Leu Leu Leu Thr Leu Arg Ala Arg Cys
            20              25              30

Leu Ser Ala Glu Pro Gly Gln Gly Ala Gln Thr Trp Ala Arg Phe Ala
        35              40              45

Arg Pro Pro Val Pro Glu Ala Ser Gly Leu Leu His Asp Thr Phe Pro
    50              55              60

Asp Gly Phe Leu Trp Ala Val Gly Ser Ala Ala Tyr Gln Thr Glu Gly
65              70              75              80

Gly Trp Arg Gln His Gly Lys Gly Ala Ser Ile Trp Asp Thr Phe Thr
                85              90              95
```

```
His His Pro Arg Ala Ile Pro Glu Asp Ser Pro Ile Val Met Ala Pro
            100                 105                 110

Ser Gly Ala Pro Leu Pro Pro Leu Pro Ser Thr Gly Asp Val Ala Ser
        115                 120                 125

Asp Ser Tyr Asn Asn Val Tyr Arg Asp Thr Glu Gly Leu Arg Glu Leu
    130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
                180                 185                 190

Leu Tyr His Trp Asp Leu Pro Gln Arg Leu Gln Asp Thr Tyr Gly Gly
            195                 200                 205

Trp Ala Asn Arg Ala Leu Ala Asp His Phe Arg Asp Tyr Ala Glu Leu
210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
            260                 265                 270

Leu Leu Leu Ala His Ala Lys Val Trp Arg Leu Tyr Asn Thr Ser Phe
            275                 280                 285

Arg Pro Thr Gln Gly Gly Arg Val Ser Ile Ala Leu Gly Ser His Trp
        290                 295                 300

Ile Thr Pro Arg Arg Met Thr Asp Tyr His Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Lys Ser Met Lys Asn Asn Leu Ser Ser Leu Leu Pro
            340                 345                 350

Asp Phe Thr Glu Ser Glu Lys Arg Phe Ile Arg Gly Thr Ala Asp Phe
        355                 360                 365

Phe Ala Leu Ser Phe Gly Pro Thr Leu Ser Phe Gln Leu Leu Asp Pro
370                 375                 380

Ser Met Lys Phe Arg Gln Leu Glu Ser Pro Ser Leu Arg Gln Leu Leu
385                 390                 395                 400

Ser Trp Ile Asp Leu Glu Tyr Asn His Pro Gln Ile Phe Ile Val Glu
                405                 410                 415

Asn Gly Trp Phe Val Ser Gly Thr Thr Arg Arg Asp Asp Ala Lys Tyr
            420                 425                 430

Met Tyr Tyr Leu Lys Lys Phe Ile Met Glu Ser Leu Lys Ala Ile Arg
        435                 440                 445

Leu Asp Gly Val Asp Val Ile Gly Tyr Thr Ala Trp Ser Leu Met Asp
450                 455                 460

Gly Phe Glu Trp His Arg Gly Tyr Ser Ile Arg Arg Gly Leu Phe Tyr
465                 470                 475                 480

Val Asp Phe Leu Ser Gln Asp Lys Glu Leu Leu Pro Lys Ser Ser Ala
                485                 490                 495

Leu Phe Tyr Gln Lys Leu Ile Glu Asn Asn Gly Phe Pro Pro Leu Pro
            500                 505                 510

Glu Asn Gln Pro Leu Glu Gly Thr Phe Pro Cys Asp Phe Ala Trp Gly
```

```
            515                 520                 525
Val Val Asp Asn Tyr Ile Gln Val Asp Pro Thr Leu Ser Gln Phe Thr
530                 535                 540

Asp Pro Asn Val Tyr Leu Trp Asp Val His His Ser Lys Arg Leu Ile
545                 550                 555                 560

Lys Val Asp Gly Val Ala Lys Lys Lys Pro Tyr Cys Val Asp
                565                 570                 575

Phe Ser Ala Ile Arg Pro Gln Ile Thr Leu Leu Arg Glu Met Arg Val
                580                 585                 590

Thr His Phe Arg Phe Ser Leu Asp Trp Ala Leu Ile Leu Pro Leu Gly
                595                 600                 605

Asn Gln Thr Gln Val Asn Arg Thr Val Leu His Phe Tyr Arg Cys Met
610                 615                 620

Val Ser Glu Leu Val His Ala Asn Ile Thr Pro Val Val Ala Leu Trp
625                 630                 635                 640

Gln Pro Ala Thr Pro His Gln Gly Leu Pro His Ala Leu Ala Lys His
                645                 650                 655

Gly Ala Trp Glu Asn Pro His Thr Ala Leu Ala Phe Ala Asp Tyr Ala
                660                 665                 670

Asn Leu Cys Phe Glu Glu Leu Gly His Trp Val Lys Phe Trp Ile Thr
                675                 680                 685

Ile Asn Glu Pro Asn Ser Arg Asn Met Thr Tyr Arg Ala Gly His His
690                 695                 700

Leu Leu Lys Ala His Ala Leu Ala Trp His Leu Tyr Asp Asp Lys Phe
705                 710                 715                 720

Arg Ala Ala Gln Lys Gly Lys Ile Ser Ile Ala Leu Gln Val Asp Trp
                725                 730                 735

Ile Glu Pro Ala Cys Pro Phe Ser Gln Lys Asp Lys Glu Val Ala Glu
                740                 745                 750

Arg Val Leu Glu Phe Asp Val Gly Trp Leu Ala Glu Pro Ile Phe Gly
                755                 760                 765

Ser Gly Asp Tyr Pro His Val Met Arg Glu Trp Leu Asn Gln Lys Asn
                770                 775                 780

Asn Phe Leu Leu Pro Tyr Phe Thr Glu Asp Glu Lys Lys Leu Ile Arg
785                 790                 795                 800

Gly Ser Phe Asp Phe Leu Ala Leu Ser His Tyr Thr Thr Ile Leu Val
                805                 810                 815

Asp Trp Glu Lys Glu Asp Pro Ile Lys Tyr Asn Asp Tyr Leu Glu Val
                820                 825                 830

Gln Glu Met Thr Asp Ile Thr Trp Leu Asn Ser Pro Asn Gln Val Ala
                835                 840                 845

Val Val Pro Trp Gly Leu Arg Lys Ala Leu Asn Trp Leu Arg Phe Lys
                850                 855                 860

Tyr Gly Asp Leu Pro Met Phe Val Thr Ala Asn Gly Ile Asp Asp
865                 870                 875                 880

Pro His Ala Glu Gln Asp Ser Leu Arg Met Tyr Tyr Ile Lys Asn Tyr
                885                 890                 895

Val Asn Glu Ala Leu Lys Ala Tyr Val Leu Asp Gly Ile Asn Leu Cys
                900                 905                 910

Gly Tyr Phe Ala Tyr Ser Leu Ser Asp Arg Ser Val Pro Lys Ser Gly
                915                 920                 925

Phe Tyr Arg Tyr Ala Ala Asn Gln Phe Glu Pro Lys Pro Ser Ile Lys
                930                 935                 940
```

His Tyr Arg Lys Ile Ile Asp Asn Asn Gly Phe Leu Gly Ser Gly Thr
945                 950                 955                 960

Leu Gly Arg Phe Cys Pro Glu Glu Tyr Thr Val Cys Thr Gly Cys Gly
                965                 970                 975

Phe Phe Gln Thr Arg Lys Ser
            980

<210> SEQ ID NO 8
<211> LENGTH: 1013
<212> TYPE: PRT
<213> ORGANISM: Macaca speciosa

<400> SEQUENCE: 8

Met Pro Ala Ser Ala Pro Pro Arg Arg Pro Arg Pro Pro Pro Pro Ser
1               5                   10                  15

Leu Ser Leu Ser Leu Leu Val Leu Gly Leu Ala Gly Arg Arg
            20                  25                  30

Leu Arg Ala Glu Pro Gly Asp Gly Ala Gln Thr Trp Ala Arg Phe Ala
            35                  40                  45

Arg Pro Pro Ala Pro Glu Ala Ala Gly Leu Phe Gln Gly Thr Phe Pro
50                  55                  60

Asp Gly Phe Leu Trp Ala Val Gly Ser Ala Ala Tyr Gln Thr Glu Gly
65                  70                  75                  80

Gly Trp Gln Gln His Gly Lys Gly Ala Ser Ile Trp Asp Thr Phe Thr
                85                  90                  95

His His Pro Leu Ala Pro Pro Gly Asp Ser Arg Ile Ala Asn Val Pro
                100                 105                 110

Ser Gly Ala Pro Ser Pro Leu Gln Pro Ala Thr Gly Asp Val Ala Ser
            115                 120                 125

Asp Ser Tyr Asn Asn Val Phe Arg Asp Thr Glu Ala Leu Arg Glu Leu
130                 135                 140

Gly Val Thr His Tyr Arg Phe Ser Ile Ser Trp Ala Arg Val Leu Pro
145                 150                 155                 160

Asn Gly Ser Ala Gly Val Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Ala Tyr Gly Gly
            195                 200                 205

Trp Ala Asn Arg Ala Leu Ala Asp His Phe Arg Asp Tyr Ala Glu Leu
210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Ile Arg Gly Ser Pro Arg Leu Gly Tyr Leu Val Ala His Asn
            260                 265                 270

Leu Leu Leu Ala His Ala Lys Val Trp His Leu Tyr Asn Thr Ser Phe
            275                 280                 285

Arg Pro Thr Gln Gly Gly Gln Val Ser Ile Ala Leu Ser Ser His Trp
290                 295                 300

Ile Asn Pro Arg Arg Met Asp His Ser Ile Lys Glu Cys Gln Lys Ser
305                 310                 315                 320

Leu Asp Phe Val Leu Gly Trp Phe Ala Lys Pro Ile Phe Ile Asp Gly

```
                325                 330                 335
Asp Tyr Pro Glu Ser Met Lys Asn Asn Leu Ser Ser Leu Leu Pro Asp
                340                 345                 350

Phe Thr Glu Ser Glu Lys Lys Phe Ile Lys Gly Thr Ala Asp Phe Phe
                355                 360                 365

Ala Leu Ser Phe Gly Pro Thr Leu Ser Phe Gln Leu Leu Asp Pro His
370                 375                 380

Met Lys Phe Arg Gln Leu Glu Ser Pro Ser Leu Arg Gln Leu Leu Ser
385                 390                 395                 400

Trp Ile Asp Leu Glu Tyr Asn His Pro Gln Ile Phe Ile Val Glu Asn
                405                 410                 415

Gly Trp Phe Val Ser Gly Thr Thr Lys Arg Asp Asp Ala Lys Tyr Met
                420                 425                 430

Tyr Tyr Leu Lys Lys Phe Ile Met Glu Thr Leu Lys Ala Ile Lys Leu
                435                 440                 445

Asp Gly Val Asp Val Ile Gly Tyr Thr Ala Trp Ser Leu Met Asp Gly
                450                 455                 460

Phe Glu Trp His Arg Gly Tyr Ser Ile Arg Arg Gly Leu Phe Tyr Val
465                 470                 475                 480

Asp Phe Leu Ser Gln Glu Lys Thr Leu Leu Pro Lys Ser Ser Ala Leu
                485                 490                 495

Phe Tyr Gln Lys Leu Ile Glu Lys Asn Gly Phe Pro Pro Leu Pro Glu
                500                 505                 510

Asn Gln Pro Leu Glu Gly Thr Phe Pro Cys Asp Phe Ala Trp Gly Ile
                515                 520                 525

Val Asp Asn Tyr Ile Gln Val Asp Thr Thr Leu Ser Gln Phe Thr Asp
                530                 535                 540

Leu Asn Val Tyr Leu Trp Asp Val His His Ser Lys Arg Leu Ile Lys
545                 550                 555                 560

Val Asp Gly Val Val Thr Lys Lys Arg Lys Ser Tyr Cys Val Asp Phe
                565                 570                 575

Ala Ala Ile Gln Pro Gln Ile Thr Leu Leu Gln Glu Met His Val Thr
                580                 585                 590

His Phe Arg Phe Ser Leu Asp Trp Ala Leu Ile Leu Pro Leu Gly Asn
                595                 600                 605

Gln Ser Gln Val Asn His Thr Ile Leu Gln Tyr Tyr Arg Cys Met Val
                610                 615                 620

Ser Glu Leu Val Arg Val Asn Ile Thr Pro Val Val Ala Leu Trp Gln
625                 630                 635                 640

Pro Val Ala Pro Asn Gln Gly Leu Pro Arg Leu Leu Ala Arg Gln Gly
                645                 650                 655

Ala Trp Glu Asn Pro Tyr Thr Ala Leu Ala Phe Ala Glu Tyr Ala Arg
                660                 665                 670

Leu Cys Phe Gln Glu Leu Gly His His Val Lys Leu Trp Ile Thr Met
                675                 680                 685

Asn Glu Pro Tyr Thr Arg Asn Met Thr Tyr Ser Ala Gly His Asn Leu
                690                 695                 700

Leu Lys Ala His Ala Leu Ala Trp His Val Tyr Asn Glu Lys Phe Arg
705                 710                 715                 720

His Ala Gln Asn Gly Lys Ile Ser Ile Ala Leu Gln Ala Asp Trp Ile
                725                 730                 735

Glu Pro Ala Cys Pro Phe Ser Gln Lys Asp Lys Glu Val Ala Glu Arg
                740                 745                 750
```

Val Leu Glu Phe Asp Ile Gly Trp Leu Ala Glu Pro Ile Phe Gly Ser
              755                 760                 765

Gly Asp Tyr Pro Trp Val Met Arg Asp Trp Leu Asn Gln Arg Asn Asn
770                 775                 780

Phe Leu Leu Pro Tyr Phe Thr Glu Asp Lys Lys Leu Ile Gln Gly
785                 790                 795                 800

Thr Phe Asp Phe Leu Ala Leu Ser His Tyr Thr Thr Ile Leu Val Asp
                805                 810                 815

Ser Glu Lys Glu Asp Pro Ile Lys Tyr Asn Asp Tyr Leu Glu Val Gln
                820                 825                 830

Glu Met Thr Asp Ile Thr Trp Leu Asn Ser Pro Ser Gln Val Ala Val
                835                 840                 845

Val Pro Trp Gly Leu Arg Lys Val Leu Asn Trp Leu Lys Phe Lys Tyr
                850                 855                 860

Gly Asp Leu Pro Met Tyr Ile Ile Ser Asn Gly Ile Asp Asp Gly Leu
865                 870                 875                 880

His Ala Glu Asp Asp Gln Leu Arg Val Tyr Tyr Met Gln Asn Tyr Ile
                885                 890                 895

Asn Glu Ala Leu Lys Ala His Ile Leu Asp Gly Ile Asn Leu Cys Gly
                900                 905                 910

Tyr Phe Ala Tyr Ser Phe Asn Asp Arg Thr Ala Pro Arg Phe Gly Leu
                915                 920                 925

Tyr Arg Phe Ala Ala Asp Gln Phe Glu Pro Lys Pro Ser Met Lys His
                930                 935                 940

Tyr Arg Lys Ile Ile Asp Ser Asn Gly Phe Pro Gly Pro Glu Thr Leu
945                 950                 955                 960

Glu Lys Phe Cys Pro Glu Glu Phe Thr Val Cys Thr Glu Cys Ser Phe
                965                 970                 975

Phe His Thr Arg Lys Pro Leu Val Ala Phe Ile Ala Phe Leu Phe Phe
                980                 985                 990

Ala Phe Ile Val Ser Leu Ser Leu Ile Phe Tyr Tyr Ser Lys Lys Gly
                995                 1000                1005

Arg Arg Arg Tyr Gln
        1010

<210> SEQ ID NO 9
<211> LENGTH: 983
<212> TYPE: PRT
<213> ORGANISM: Macaca speciosa

<400> SEQUENCE: 9

Met Pro Ala Ser Ala Pro Pro Arg Arg Pro Arg Pro Pro Pro Ser
1                   5                   10                  15

Leu Ser Leu Ser Leu Leu Leu Val Leu Gly Leu Ala Gly Arg Arg
                20                  25                  30

Leu Arg Ala Glu Pro Gly Asp Gly Ala Gln Thr Trp Ala Arg Phe Ala
                35                  40                  45

Arg Pro Pro Ala Pro Glu Ala Ala Gly Leu Phe Gln Gly Thr Phe Pro
50                  55                  60

Asp Gly Phe Leu Trp Ala Val Gly Ser Ala Ala Tyr Gln Thr Glu Gly
65                  70                  75                  80

Gly Trp Gln Gln His Gly Lys Gly Ala Ser Ile Trp Asp Thr Phe Thr
                85                  90                  95

His His Pro Leu Ala Pro Pro Gly Asp Ser Arg Ile Ala Asn Val Pro

```
            100                 105                 110
Ser Gly Ala Pro Ser Pro Leu Gln Pro Ala Thr Gly Asp Val Ala Ser
        115                 120                 125

Asp Ser Tyr Asn Asn Val Phe Arg Asp Thr Glu Ala Leu Arg Glu Leu
130                 135                 140

Gly Val Thr His Tyr Arg Phe Ser Ile Ser Trp Ala Arg Val Leu Pro
145                 150                 155                 160

Asn Gly Ser Ala Gly Val Pro Asn Arg Glu Gly Leu Arg Tyr Tyr Arg
                165                 170                 175

Arg Leu Leu Glu Arg Leu Arg Glu Leu Gly Val Gln Pro Val Val Thr
                180                 185                 190

Leu Tyr His Trp Asp Leu Pro Gln Arg Leu Gln Asp Ala Tyr Gly Gly
                195                 200                 205

Trp Ala Asn Arg Ala Leu Ala Asp His Phe Arg Asp Tyr Ala Glu Leu
210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Ile Arg Gly Ser Pro Arg Leu Gly Tyr Leu Val Ala His Asn
                260                 265                 270

Leu Leu Leu Ala His Ala Lys Val Trp His Leu Tyr Asn Thr Ser Phe
                275                 280                 285

Arg Pro Thr Gln Gly Gly Gln Val Ser Ile Ala Leu Ser Ser His Trp
                290                 295                 300

Ile Asn Pro Arg Arg Met Thr Asp His Ser Ile Lys Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
                340                 345                 350

Asp Phe Thr Glu Ser Glu Lys Lys Phe Ile Lys Gly Thr Ala Asp Phe
                355                 360                 365

Phe Ala Leu Ser Phe Gly Pro Thr Leu Ser Phe Gln Leu Leu Asp Pro
370                 375                 380

His Met Lys Phe Arg Gln Leu Glu Ser Pro Ser Leu Arg Gln Leu Leu
385                 390                 395                 400

Ser Trp Ile Asp Leu Glu Tyr Asn His Pro Gln Ile Phe Ile Val Glu
                405                 410                 415

Asn Gly Trp Phe Val Ser Gly Thr Thr Lys Arg Asp Asp Ala Lys Tyr
                420                 425                 430

Met Tyr Tyr Leu Lys Lys Phe Ile Met Glu Thr Leu Lys Ala Ile Lys
                435                 440                 445

Leu Asp Gly Val Asp Val Ile Gly Tyr Thr Ala Trp Ser Leu Met Asp
                450                 455                 460

Gly Phe Glu Trp His Arg Gly Tyr Ser Ile Arg Arg Gly Leu Phe Tyr
465                 470                 475                 480

Val Asp Phe Leu Ser Gln Glu Lys Thr Leu Leu Pro Lys Ser Ser Ala
                485                 490                 495

Leu Phe Tyr Gln Lys Leu Ile Glu Lys Asn Gly Phe Pro Pro Leu Pro
                500                 505                 510

Glu Asn Gln Pro Leu Glu Gly Thr Phe Pro Cys Asp Phe Ala Trp Gly
                515                 520                 525
```

```
Ile Val Asp Asn Tyr Ile Gln Val Asp Thr Thr Leu Ser Gln Phe Thr
530                 535                 540

Asp Leu Asn Val Tyr Leu Trp Asp Val His His Ser Lys Arg Leu Ile
545                 550                 555                 560

Lys Val Asp Gly Val Val Thr Lys Arg Lys Ser Tyr Cys Val Asp
                565                 570                 575

Phe Ala Ala Ile Gln Pro Gln Ile Thr Leu Leu Gln Glu Met His Val
                580                 585                 590

Thr His Phe Arg Phe Ser Leu Asp Trp Ala Leu Ile Leu Pro Leu Gly
                595                 600                 605

Asn Gln Ser Gln Val Asn His Thr Ile Leu Gln Tyr Tyr Arg Cys Met
610                 615                 620

Val Ser Glu Leu Val Arg Val Asn Ile Thr Pro Val Ala Leu Trp
625                 630                 635                 640

Gln Pro Val Ala Pro Asn Gln Gly Leu Pro Arg Leu Leu Ala Arg Gln
                645                 650                 655

Gly Ala Trp Glu Asn Pro Tyr Thr Ala Leu Ala Phe Ala Glu Tyr Ala
                660                 665                 670

Arg Leu Cys Phe Gln Glu Leu Gly His His Val Lys Leu Trp Ile Thr
                675                 680                 685

Met Asn Glu Pro Tyr Thr Arg Asn Met Thr Tyr Ser Ala Gly His Asn
690                 695                 700

Leu Leu Lys Ala His Ala Leu Ala Trp His Val Tyr Asn Glu Lys Phe
705                 710                 715                 720

Arg His Ala Gln Asn Gly Lys Ile Ser Ile Ala Leu Gln Ala Asp Trp
                725                 730                 735

Ile Glu Pro Ala Cys Pro Phe Ser Gln Lys Asp Lys Glu Val Ala Glu
                740                 745                 750

Arg Val Leu Glu Phe Asp Ile Gly Trp Leu Ala Glu Pro Ile Phe Gly
                755                 760                 765

Ser Gly Asp Tyr Pro Trp Val Met Arg Asp Trp Leu Asn Gln Arg Asn
770                 775                 780

Asn Phe Leu Leu Pro Tyr Phe Thr Glu Asp Glu Lys Lys Leu Ile Gln
785                 790                 795                 800

Gly Thr Phe Asp Phe Leu Ala Leu Ser His Tyr Thr Thr Ile Leu Val
                805                 810                 815

Asp Ser Glu Lys Glu Asp Pro Ile Lys Tyr Asn Asp Tyr Leu Glu Val
                820                 825                 830

Gln Glu Met Thr Asp Ile Thr Trp Leu Asn Ser Pro Ser Gln Val Ala
                835                 840                 845

Val Val Pro Trp Gly Leu Arg Lys Val Leu Asn Trp Leu Lys Phe Lys
850                 855                 860

Tyr Gly Asp Leu Pro Met Tyr Ile Ile Ser Asn Gly Ile Asp Asp Gly
865                 870                 875                 880

Leu His Ala Glu Asp Gln Leu Arg Val Tyr Met Gln Asn Tyr
                885                 890                 895

Ile Asn Glu Ala Leu Lys Ala His Ile Leu Asp Gly Ile Asn Leu Cys
                900                 905                 910

Gly Tyr Phe Ala Tyr Ser Phe Asn Asp Arg Thr Ala Pro Arg Phe Gly
                915                 920                 925

Leu Tyr Arg Phe Ala Ala Asp Gln Phe Glu Pro Lys Pro Ser Met Lys
930                 935                 940
```

-continued

```
His Tyr Arg Lys Ile Ile Asp Ser Asn Gly Phe Pro Gly Pro Glu Thr
945                 950                 955                 960

Leu Glu Lys Phe Cys Pro Glu Glu Phe Thr Val Cys Thr Glu Cys Ser
            965                 970                 975

Phe Phe His Thr Arg Lys Pro
            980

<210> SEQ ID NO 10
<211> LENGTH: 954
<212> TYPE: PRT
<213> ORGANISM: Artificial Sequence
<220> FEATURE:
<223> OTHER INFORMATION: Synthetic Construct

<400> SEQUENCE: 10

Glu Pro Gly Gln Gly Ala Gln Thr Trp Ala Arg Phe Ala Arg Ala Pro
1               5                   10                  15

Ala Pro Glu Ala Ala Gly Leu Leu His Asp Thr Phe Pro Asp Gly Phe
            20                  25                  30

Leu Trp Ala Val Gly Ser Ala Ala Tyr Gln Thr Glu Gly Gly Trp Arg
        35                  40                  45

Gln His Gly Lys Gly Ala Ser Ile Trp Asp Thr Phe Thr His His Ser
    50                  55                  60

Gly Ala Ala Pro Ser Asp Ser Pro Ile Val Val Ala Pro Ser Gly Ala
65                  70                  75                  80

Pro Ser Pro Pro Leu Ser Ser Thr Gly Asp Val Ala Ser Asp Ser Tyr
                85                  90                  95

Asn Asn Val Tyr Arg Asp Thr Glu Gly Leu Arg Glu Leu Gly Val Thr
            100                 105                 110

His Tyr Arg Phe Ser Ile Ser Trp Ala Arg Val Leu Pro Asn Gly Thr
        115                 120                 125

Ala Gly Thr Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Thr Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Val
    210                 215                 220

Arg Gly Ser Ser Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Arg Val Ser Ile Ala Leu Ser Ser His Trp Ile Asn Pro
            260                 265                 270

Arg Arg Met Thr Asp Tyr Asn Ile Arg Glu Cys Gln Lys Ser Leu Asp
        275                 280                 285

Phe Val Leu Gly Trp Phe Ala Lys Pro Ile Phe Ile Asp Gly Asp Tyr
    290                 295                 300

Pro Glu Ser Met Lys Asn Asn Leu Ser Ser Leu Leu Pro Asp Phe Thr
305                 310                 315                 320
```

```
Glu Ser Glu Lys Arg Leu Ile Arg Gly Thr Ala Asp Phe Phe Ala Leu
                325                 330                 335

Ser Phe Gly Pro Thr Leu Ser Phe Gln Leu Leu Asp Pro Asn Met Lys
        340                 345                 350

Phe Arg Gln Leu Glu Ser Pro Asn Leu Arg Gln Leu Leu Ser Trp Ile
            355                 360                 365

Asp Leu Glu Tyr Asn His Pro Pro Ile Phe Ile Val Glu Asn Gly Trp
        370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Arg Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Glu Leu Leu Pro Lys Ser Ala Leu Phe Tyr
        450                 455                 460

Gln Lys Leu Ile Glu Asp Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Val Gln Val Asp Thr Thr Leu Ser Gln Phe Thr Asp Pro Asn
            500                 505                 510

Val Tyr Leu Trp Asp Val His His Ser Lys Arg Leu Ile Lys Val Asp
        515                 520                 525

Gly Val Val Ala Lys Lys Arg Lys Pro Tyr Cys Val Asp Phe Ser Ala
        530                 535                 540

Ile Arg Pro Gln Ile Thr Leu Leu Arg Glu Met Arg Val Thr His Phe
545                 550                 555                 560

Arg Phe Ser Leu Asp Trp Ala Leu Ile Leu Pro Leu Gly Asn Gln Thr
                565                 570                 575

Gln Val Asn His Thr Val Leu His Phe Tyr Arg Cys Met Ile Ser Glu
            580                 585                 590

Leu Val His Ala Asn Ile Thr Pro Val Val Ala Leu Trp Gln Pro Ala
        595                 600                 605

Ala Pro His Gln Gly Leu Pro His Ala Leu Ala Lys His Gly Ala Trp
        610                 615                 620

Glu Asn Pro His Thr Ala Leu Ala Phe Ala Asp Tyr Ala Asn Leu Cys
625                 630                 635                 640

Phe Lys Glu Leu Gly His Trp Val Asn Leu Trp Ile Thr Met Asn Glu
                645                 650                 655

Pro Asn Thr Arg Asn Met Thr Tyr Arg Ala Gly His His Leu Leu Arg
            660                 665                 670

Ala His Ala Leu Ala Trp His Leu Tyr Asp Asp Lys Phe Arg Ala Ala
        675                 680                 685

Gln Lys Gly Lys Ile Ser Ile Ala Leu Gln Ala Asp Trp Ile Glu Pro
        690                 695                 700

Ala Cys Pro Phe Ser Gln Asn Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Arg Val Met Arg Asp Trp Leu Asn Gln Lys Asn Asn Phe Leu
```

```
            740                 745                 750
Leu Pro Tyr Phe Thr Glu Asp Glu Lys Lys Leu Val Arg Gly Ser Phe
        755                 760                 765

Asp Phe Leu Ala Val Ser His Tyr Thr Thr Ile Leu Val Asp Trp Glu
    770                 775                 780

Lys Glu Asp Pro Met Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Arg Phe Lys Tyr Gly Asp
                820                 825                 830

Leu Pro Met Tyr Val Thr Ala Asn Gly Ile Asp Asp Pro His Ala
            835                 840                 845

Glu Gln Asp Ser Leu Arg Ile Tyr Tyr Ile Lys Asn Tyr Val Asn Glu
    850                 855                 860

Ala Leu Lys Ala Tyr Val Leu Asp Asp Ile Asn Leu Cys Gly Tyr Phe
865                 870                 875                 880

Ala Tyr Ser Leu Ser Asp Arg Ser Ala Pro Lys Ser Gly Phe Tyr Arg
                885                 890                 895

Tyr Ala Ala Asn Gln Phe Glu Pro Lys Pro Ser Met Lys His Tyr Arg
                900                 905                 910

Arg Ile Ile Asp Ser Asn Gly Phe Leu Gly Ser Gly Thr Leu Gly Arg
                915                 920                 925

Phe Cys Pro Glu Glu Tyr Thr Val Cys Thr Glu Cys Gly Phe Phe Gln
    930                 935                 940

Thr Arg Lys Ser His His His His His His
945                 950

<210> SEQ ID NO 11
<211> LENGTH: 948
<212> TYPE: PRT
<213> ORGANISM: Mus musculus

<400> SEQUENCE: 11

Glu Pro Gly Gln Gly Ala Gln Thr Trp Ala Arg Phe Arg Ala Pro
1               5                   10                  15

Ala Pro Glu Ala Ala Gly Leu Leu His Asp Thr Phe Pro Asp Gly Phe
                20                  25                  30

Leu Trp Ala Val Gly Ser Ala Ala Tyr Gln Thr Glu Gly Gly Trp Arg
            35                  40                  45

Gln His Gly Lys Gly Ala Ser Ile Trp Asp Thr Phe Thr His His Ser
        50                  55                  60

Gly Ala Ala Pro Ser Asp Ser Pro Ile Val Val Ala Pro Ser Gly Ala
65                  70                  75                  80

Pro Ser Pro Pro Leu Ser Ser Thr Gly Asp Val Ala Ser Asp Ser Tyr
                85                  90                  95

Asn Asn Val Tyr Arg Asp Thr Glu Gly Leu Arg Glu Leu Gly Val Thr
            100                 105                 110

His Tyr Arg Phe Ser Ile Ser Trp Ala Arg Val Leu Pro Asn Gly Thr
        115                 120                 125

Ala Gly Thr Pro Asn Arg Glu Gly Leu Arg Tyr Tyr Arg Arg Leu Leu
    130                 135                 140
```

```
Glu Arg Leu Arg Glu Leu Gly Val Gln Pro Val Thr Leu Tyr His
145                 150                 155                 160

Trp Asp Leu Pro Gln Arg Leu Gln Asp Thr Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Val
    210                 215                 220

Arg Gly Ser Ser Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Arg Val Ser Ile Ala Leu Ser Ser His Trp Ile Asn Pro
            260                 265                 270

Arg Arg Met Thr Asp Tyr Asn Ile Arg Glu Cys Gln Lys Ser Leu Asp
        275                 280                 285

Phe Val Leu Gly Trp Phe Ala Lys Pro Ile Phe Ile Asp Gly Asp Tyr
    290                 295                 300

Pro Glu Ser Met Lys Asn Asn Leu Ser Ser Leu Leu Pro Asp Phe Thr
305                 310                 315                 320

Glu Ser Glu Lys Arg Leu Ile Arg Gly Thr Ala Asp Phe Phe Ala Leu
                325                 330                 335

Ser Phe Gly Pro Thr Leu Ser Phe Gln Leu Leu Asp Pro Asn Met Lys
            340                 345                 350

Phe Arg Gln Leu Glu Ser Pro Asn Leu Arg Gln Leu Leu Ser Trp Ile
        355                 360                 365

Asp Leu Glu Tyr Asn His Pro Pro Ile Phe Ile Val Glu Asn Gly Trp
    370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Arg Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Glu Leu Leu Pro Lys Ser Ser Ala Leu Phe Tyr
    450                 455                 460

Gln Lys Leu Ile Glu Asp Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Val Gln Val Asp Thr Thr Leu Ser Gln Phe Thr Asp Pro Asn
            500                 505                 510

Val Tyr Leu Trp Asp Val His His Ser Lys Arg Leu Ile Lys Val Asp
        515                 520                 525

Gly Val Val Ala Lys Lys Arg Lys Pro Tyr Cys Val Asp Phe Ser Ala
    530                 535                 540

Ile Arg Pro Gln Ile Thr Leu Leu Arg Glu Met Arg Val Thr His Phe
545                 550                 555                 560
```

```
Arg Phe Ser Leu Asp Trp Ala Leu Ile Leu Pro Leu Gly Asn Gln Thr
                565                 570                 575

Gln Val Asn His Thr Val Leu His Phe Tyr Arg Cys Met Ile Ser Glu
            580                 585                 590

Leu Val His Ala Asn Ile Thr Pro Val Val Ala Leu Trp Gln Pro Ala
        595                 600                 605

Ala Pro His Gln Gly Leu Pro His Ala Leu Ala Lys His Gly Ala Trp
    610                 615                 620

Glu Asn Pro His Thr Ala Leu Ala Phe Ala Asp Tyr Ala Asn Leu Cys
625                 630                 635                 640

Phe Lys Glu Leu Gly His Trp Val Asn Leu Trp Ile Thr Met Asn Glu
                645                 650                 655

Pro Asn Thr Arg Asn Met Thr Tyr Arg Ala Gly His His Leu Leu Arg
            660                 665                 670

Ala His Ala Leu Ala Trp His Leu Tyr Asp Asp Lys Phe Arg Ala Ala
        675                 680                 685

Gln Lys Gly Lys Ile Ser Ile Ala Leu Gln Ala Asp Trp Ile Glu Pro
    690                 695                 700

Ala Cys Pro Phe Ser Gln Asn Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Arg Val Met Arg Asp Trp Leu Asn Gln Lys Asn Asn Phe Leu
            740                 745                 750

Leu Pro Tyr Phe Thr Glu Asp Glu Lys Lys Leu Val Arg Gly Ser Phe
        755                 760                 765

Asp Phe Leu Ala Val Ser His Tyr Thr Thr Ile Leu Val Asp Trp Glu
    770                 775                 780

Lys Glu Asp Pro Met Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Arg Phe Lys Tyr Gly Asp
            820                 825                 830

Leu Pro Met Tyr Val Thr Ala Asn Gly Ile Asp Asp Pro His Ala
        835                 840                 845

Glu Gln Asp Ser Leu Arg Ile Tyr Tyr Ile Lys Asn Tyr Val Asn Glu
850                 855                 860

Ala Leu Lys Ala Tyr Val Leu Asp Asp Ile Asn Leu Cys Gly Tyr Phe
865                 870                 875                 880

Ala Tyr Ser Leu Ser Asp Arg Ser Ala Pro Lys Ser Gly Phe Tyr Arg
                885                 890                 895

Tyr Ala Ala Asn Gln Phe Glu Pro Lys Pro Ser Met Lys His Tyr Arg
            900                 905                 910

Lys Ile Ile Asp Ser Asn Gly Phe Leu Gly Ser Gly Thr Leu Gly Arg
        915                 920                 925

Phe Cys Pro Glu Glu Tyr Thr Val Cys Thr Glu Cys Gly Phe Phe Gln
    930                 935                 940

Thr Arg Lys Ser
945
```